(12) United States Patent
Larsen et al.

(10) Patent No.: US 7,749,969 B2
(45) Date of Patent: Jul. 6, 2010

(54) N- OR C- TERMINALLY MODIFIED SMALL PEPTIDES

(75) Inventors: Bjarne Due Larsen, Roskilde (DK); Edward H. Kerns, Skillman, NJ (US)

(73) Assignees: Zealand Pharma A/S, Glostrup (DK); Wyeth, Madison, NJ (US)

( * ) Notice: Subject to any disclaimer, the term of this patent is extended or adjusted under 35 U.S.C. 154(b) by 815 days.

(21) Appl. No.: 11/482,365

(22) Filed: Jul. 7, 2006

(65) Prior Publication Data

US 2007/0123469 A1      May 31, 2007

Related U.S. Application Data

(60) Provisional application No. 60/697,138, filed on Jul. 7, 2005.

(51) Int. Cl.
*A61K 38/05*      (2006.01)
*C07K 5/06*      (2006.01)

(52) U.S. Cl. ............................................. 514/19; 514/2

(58) Field of Classification Search ....................... None
See application file for complete search history.

(56) References Cited

U.S. PATENT DOCUMENTS

| 3,976,771 | A | | 8/1976 | Lindberg et al. | |
|---|---|---|---|---|---|
| 5,780,498 | A | * | 7/1998 | Saika et al. ................. | 514/419 |
| 7,250,397 | B2 | | 7/2007 | Larsen et al. | |
| 2005/0075280 | A1 | | 4/2005 | Larsen et al. | |
| 2006/0194947 | A1 | | 8/2006 | Larsen et al. | |

FOREIGN PATENT DOCUMENTS

| WO | WO 98/11125 A1 | 3/1998 |
|---|---|---|
| WO | WO 01/62775 A2 | 8/2001 |
| WO | WO 02/077017 A2 | 10/2002 |
| WO | WO 03/063891 A1 | 8/2003 |
| WO | WO 2004/048400 A1 | 6/2004 |

OTHER PUBLICATIONS

File HCAPLUS on STN. An No: 1990:179838. Barlos et al. 'Esterfication of Partially Protected Peptide Fragments With Resins. Tetrahedron Letters (1989), vol. 30, No. 30, pp. 3947-3950. STN entry date May 1990. Abstract only with registry information.*
Larsen and Holm, "Incomplete Fmoc Deprotection in Solid-Phase Synthesis of Peptides," *Int. J. Pept. Protein Res.* 43:1-9 (1994).
Lynch et al., "Effects of 2-Substituted 3-Dimethylamino-5,6-Methylenedioxyindenes on Calcium-Induced Arrhythmias," *J. Cardiovasc. Pharmacol.* 3:49-60 (1981).
Meier et al., "Pharmacological In Vitro Characterization of the Arecoline Bioisostere, Lu 25-109-T, a Muscarinic Compound with $M_1$-Agonistic and $M_2/M_3$-Antagonistic Properties," *Drug Develop. Res.* 40:1-16 (1997).
Corey et al., "Metal-ion Sensitive Protecting Groups in Synthesis. The Carbo-(8-quinoloxy) Substituent and Its Removal by Accelerated Hydrolysis," *J. Am. Chem. Soc.* 84:4899-4904 (1962).
Deigin et al., "Reciprocal Effect of Optical Isomerism of EW-dipeptides on Immune Response," *Immunol. Lett.* 67:41-46 (1999).
Haworth et al., "The Action of Formaldehyde on Proteins. Part II. Some Reactions of N-Hydroxymethylamides," J. Chem. Soc. 2972-2980 (1952).
Lindberg et al., "Potential Antiarrhythmic Agents II. Antiarrhythmic Activity of Basic N-(Substituted Phenyl and Benzyl)dipeptides," *Acta. Pharma. Suec.* 22:321-334 (1985).
Midura-Nowaczek et al., "Synthesis of Benzylamides of Dipeptides as Potential Inhibitors of Plasmin," *Pharmazie* 58:687-689 (2003).
Schröder et al., "Über Peptidsynthesen, XI. Synthese von α-Hydroxy-lsovaleryl-Aminosäuren Und -Peptiden," 655:211-218 (1962).
Shimohigashi et al., "Chymotrypsin Inhibitory Conformation Induced by Amino Acid Side Chain-Side Chain Intramolecular CH/π Interaction," *J. Chem. Soc. Perkin Trans.*1:2479-2485 (1996).
International Search Report from PCT/GB2006/002527 dated Dec. 21, 2006.

* cited by examiner

*Primary Examiner*—Anish Gupta
(74) *Attorney, Agent, or Firm*—Clark & Elbing LLP; Kristina Bieker-Brady

(57) ABSTRACT

N- or C-terminally modified small peptides having antiarrhythmic properties are disclosed, and in particular small peptides that possess improved pharmacokinetic properties such as having a reduced tendency to inhibit the activity of isozyme 3A4 of cytochrome P 450 oxidase. The invention further relates to uses of said compounds in the preparation of a medicament, and to pharmaceutical compositions comprising said compounds.

12 Claims, No Drawings

N- OR C- TERMINALLY MODIFIED SMALL PEPTIDES

CROSS-REFERENCE TO RELATED APPLICATIONS

This application claims the benefit of U.S. provisional application No. 60/697,138, filed Jul. 7, 2005, and British patent application No. GB0514071.0, filed Jul. 7, 2005, each of which is hereby incorporated by reference.

FIELD OF THE INVENTION

The invention relates to modified peptides having pharmacological activity, such as antiarrhythmic activity, and desirable pharmacokinetic properties compared to known antiarrhythmic dipeptides. The invention further relates to pharmaceutical compositions comprising said compounds.

BACKGROUND OF THE INVENTION

Various dipeptide derivatives described in WO 2004/048400 show antiarrhythmic activity which is comparable to the antiarrhythmic activity of an antiarrhythmic peptide, such as an AAP, AAP10, HP5 peptide compound or functional analogue thereof. Said dipeptide compounds have been shown to increase the time to an AV block in a mouse after infusion of $CaCl_2$, in what is referred to herein as a "standard calcium-induced arrhythmia assay." This increase in time has been shown to be substantially the same as for AAP, i.e., these prior art compounds show time lags of approximately the same duration. However, AAP, as well as certain AAP derivatives, are thought to have some undesired features, e.g., low stability and a need for high doses before therapeutic efficacy is achieved. Moreover, the compounds of WO 2004/048400 have been shown to inhibit the activity of isozyme 3A4 of cytochrome P 450 oxidase, which is an important drug metabolising enzyme in mammals. As these compounds are often administered to patients in combination with other drugs, inhibition of the P450 oxidase by the antiarrhythmic has the potentially undesirable effect of altering the physiological effect of the other drugs.

SUMMARY OF THE INVENTION

Broadly, the present invention relates to N- or C-terminally modified small peptides having antiarrhythmic properties, and in particular to small peptides that also possess improved pharmacokinetic properties such as have a reduced tendency to inhibit the activity of isozyme 3A4 of cytochrome P 450 oxidase. The N-terminal modified small peptides include peptides with an N-terminal carbonyl group such as an alkylcarbonyl, alkoxyalkylcarbonyl, arylcarbonyl, aryloxycarbonyl, arylalkoxycarbonyl, polycyclic carbonyl, polycyclic oxycarbonyl, or polycyclic alkoxycarbonyl group, optionally substituted with one or more substituents as defined herein. Possible N-terminal groups include a hydroxyacetyl, thiohydroxyacetyl, methoxyacetyl or acetyl(hydroxy)acetyl group. The C-terminal modified small peptides include peptides with C-terminal hydrophobic groups, such as optionally substituted aromatic or heteroaromatic groups.

In a first aspect, the present invention relates to N- or C-terminally modified small peptides represented by the following general formula I:

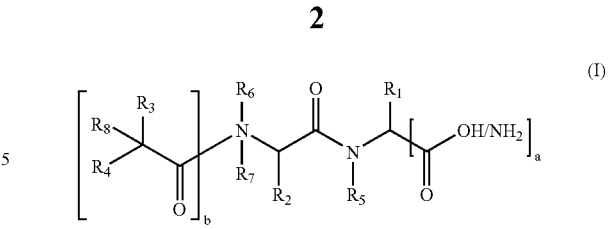

wherein:

a and b independently is 0 or 1, and if a is 0 then b is 1 or if a is 1 then b is 0, and wherein $R_2$ is any amino acid side chain, preferably Gly, Ala, Leu, Val, Ile, Nle, Nva, Lys, Orn, Dab, Dapa, Arg, Asn, Gln, Asp, Glu, Tyr, His, Trp or Phe; and $R_5$ is H or Me with the proviso that when a is 1 then $R_1$ is any amino acid side chain, preferably Tyr, Phe, His, Trp, Nal, Gly, Ala, Leu, Val, Ile, Nle, Nva, Asp, Asn, Glu or Gln; and when a is 0 then $R_1$ is an optionally substituted aromatic group which comprises an aromatic carbon or heteroaromatic ring system; and when b is 0 then $R_7$ is H or Me; and $R_6$ is an arylcarbonyl, aryloxycarbonyl, arylalkoxycarbonyl, polycyclic carbonyl, polycyclic oxycarbonyl or polycyclic alkoxycarbonyl group, optionally substituted with one or more substituents as defined herein;

and when b is 1 then $R_3$ is H, $NH_2$, OH, SH, RO, RS, RSO, $RSO_2$, COR, CSR, COOH, COOR, $CONH_2$, CONHR, $CON(R)_2$, OCOR, SCOR, or an optionally substituted phenyl or benzyl group, and $R_4$ is H, or any amino acid side chain, preferably Ala, Ser, Thr, Leu, Ile, Val, Met, Nle or Nva, and $R_6$ is H or Me, and $R_7$ is missing, and $R_8$ is H, alkyl, cycloalkyl, aryl or aralkyl; or a pharmaceutically acceptable salt thereof.

In one aspect, the present invention relates to N- or C-terminally modified small peptides represented by the following general formula IV:

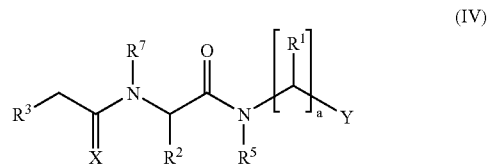

or a pharmaceutically acceptable salt thereof, wherein:
a is 0 or 1;
$R^1$ is hydrogen or an amino acid side chain;

$R^2$ is an amino acid side chain;

$R^3$ is selected from the group consisting of $OR^8$, $N(R^8)_2$, optionally substituted aryl, optionally substituted heteroaryl, and an optionally substituted polycyclic group;

$R^5$ is H or $C_{1-6}$alkyl;

$R^7$ is H or $C_{1-6}$alkyl;

$R^8$, at each occurrence, independently is selected from the group consisting of H, $C_{1-6}$alkyl, and $C(O)C_{1-6}$alkyl;

X is O or S; and

Y is selected from the group consisting of $C(O)OR^8$, $C(O)N(R^8)_2$, optionally substituted aryl, optionally substituted heteroaryl, and an optionally substituted polycyclic group;

provided that:

when Y is $C(O)OR^8$ or $C(O)N(R^8)_2$, then a is 1 and $R^1$ is an amino acid side chain;

when a is 1, Y is $C(O)NH_2$, $R^1$ is the side chain of Tyr, X is O, and $R^3$ is $N(R^8)_2$, then $R^8$ is not acetyl, hydroxyacetyl or thiohydroxyacetyl; and when a is 0, Y is substituted aryl, X is O, and $R^3$ is $N(R^8)_2$, then $R^8$ is not acetyl, hydroxyacetyl or thiohydroxyacetyl.

The compounds of the invention possess desirable pharmacokinetic properties, such as a reduced tendency of inhibition of cytochrome P 450 oxidase 3A4 and/or a reduced ability to cross the blood brain barrier, as well as being antiarrhythmic and showing other desirable pharmacological activities.

In a further aspect, the present invention provides a compound as defined herein for use in therapy.

In a further aspect, the present invention provides the use of a compound as defined herein for the preparation of a medicament for treatment of a cardiovascular condition or other disease or ailment such as osteoporosis. The medicament may be administered prophylactically or therapeutically to an individual having, or at risk of developing, said condition or disease. Administration may be parenteral, or via the nasal or oral routes. In one preferred aspect, an individual is a human being.

In a further aspect, the present invention provides a method of administering to an individual having, or at risk of developing, a cardiovascular condition or other disease or ailment, a therapeutically effective amount of any of the compounds described above. Administration may be parenteral, or via the nasal or oral routes. In one preferred aspect, an individual is a human being.

Examples of conditions which can be treated include, but are not limited to, cardiovascular disease, osteoporosis, inflammation of airway epithelium, disorders of alveolar tissue, bladder incontinence, impaired hearing due to diseases of the cochlea, endothelial lesions, diabetic retinopathy and diabetic neuropathy, ischemia of the central nervous system and spinal cord, dental tissue disorders including periodontal disease, kidney diseases, failures of bone marrow transplantation, wounds, erectile dysfunction, urinary bladder incontinence, neuropathic pain, subchronic and chronic inflammation, cancer and failures of bone marrow and stem cell transplantation, conditions which arise during transplantation of cells and tissues or during medical procedures such as surgery; as well as conditions caused by an excess of reactive oxygen species and/or free radicals and/or nitric oxide.

The present invention additionally provides pharmaceutical compositions suitable for use in the methods described above, comprising any of the compounds described above and a pharmaceutically acceptable carrier. Preferably, the carrier is sterile, pyrogen-free and virus-free.

DETAILED DESCRIPTION OF THE INVENTION

Unless specified otherwise, the following definitions are provided for specific terms, which are used in the description.

Throughout the description and claims the three-letter code for natural amino acids is used as well as generally accepted three letter codes for other α-amino acids, such as Sarcosin (Sar). Where the L or D form has not been specified, it is to be understood that the amino acid in question can be either the L or D form.

The term "peptide" herein designates any molecule comprising a chain of amino acids that are linked by means of a peptide bond. The term thus embraces molecules that include moieties that are not amino acids, but it will be understood that the peptides presented in the present specification and claims predominantly consists of amino acids that are joined by means of peptide bonds.

The term "amino acid" refers to a molecule having the general formula $R—C(NH_2)—COOH$ which is capable of forming a peptide bond with another molecule having the same general formula. The term embraces both L and D amino acids.

The term "amino acid" also refers to a molecule having the general formula NHR—CHR'—COOH (wherein R and R' together with the carbon and nitrogen to which they are bonded form a ring, e.g., proline) which is capable of forming a peptide bond with one or more other molecules having the same general formula. The term embraces both L and D amino acids.

A "naturally occurring amino acid" is in the present context one of the 20 amino acids Group Ala (A), Cys (C), Ser (S), Thr (T), Asp (D), Glu (E), Asn (N), Gln (Q), His (H), Arg (R), Lys (K), Ile (I), Leu (L), Met (M), Val (V), Phe (F), Tyr (Y), Trp (W), Gly (G), and Pro (P). Normally, these are L-amino acids, but the present invention also allows for the use of these amino acids in their D-form. Other L-amino acids used herein are Nal (2-naphthyl-L-alanine), Nle (norleucine), Nva (norvaline), Orn (ornithine), Dab (diaminobutyric acid), Dapa (7,8 diaminopelargonic acid). The present invention also allows for the use of these amino acids in their D-form.

By "functional analogues or derivatives or modified forms" of a compound is meant any chemical entity or compound which has a structural conformation and/or binding properties that are sufficiently similar to the endogenous AAP or a functional analogue thereof (e.g., such as AAP10 or HP5) or which binds to a receptor bound by AAP to provide one or more of the beneficial effects of maintaining or normalizing gap junction function (i.e., enhancing when gap junction communication is impaired or inhibiting when gap junction communication is over-stimulated or uncontrolled). Preferably, such analogues or derivatives are also able to bind to the compound carrier hPepT1 or a structural analogue thereof. As used throughout the specification and claims, the term "compound" is inclusive of a compound, or a functional analogue or derivative of such a compound as defined above.

The term "halogen" refers to F, Cl, Br, and I, where F and I are preferred.

The term "alkyl" refers to univalent groups derived from alkanes by removal of a hydrogen atom from any carbon atom: $C_nH_{2n+1}$—. The groups derived by removal of a hydrogen atom from a terminal carbon atom of unbranched alkanes form a subclass of normal alkyl (n-alkyl) groups: $H[CH_2]_n$—. The groups $RCH_2$—, $R_2CH$— (R not equal to H), and $R_3C$— (R not equal to H) are primary, secondary and tertiary alkyl groups respectively. C(1-22)alkyl refers to any alkyl group having from 1 to 22 carbon atoms and includes C(1-6)alkyl, such as methyl, ethyl, propyl, iso-propyl, butyl, pentyl and hexyl and all possible isomers thereof.

The term "alkyl," as used herein either alone or as part of another group, refers to a substituted or unsubstituted aliphatic hydrocarbon chain that may be straight-chain or branched. Examples of alkyl groups include methyl (Me), ethyl (Et), propyl (e.g., n-propyl and isopropyl), butyl (e.g., n-butyl, isobutyl, s-butyl, t-butyl), pentyl groups (e.g., n-pentyl, isopentyl, neopentyl) and the like. Preferred alkyl groups are $C_{1-10}$ alkyl and more preferably $C_{1-6}$ alkyl. Specifically included within the definition of "alkyl" are those aliphatic hydrocarbon chains that are optionally substituted.

By the phrase "lower", for example in "lower alkyl", is meant a linear, branched or cyclic chain having less than about 6 or 7 carbon atoms, for example a methyl, ethyl, propyl, cyclopropyl or butyl group.

The phrase "lower alkyl" refers to a linear or branched alkyl having less than about 6 carbon atoms, for example, methyl, ethyl, propyl (e.g., n-propyl and isopropyl), or butyl (e.g., n-butyl, isobutyl, s-butyl, t-butyl).

The term "alkenyl" refers to a straight or branched or cyclic hydrocarbon group containing one or more carbon-carbon double bonds. C(2-22)alkenyl refers to any alkenyl group having from 1 to 22 carbon atoms and includes C(2-6)alkenyl, vinyl, allyl, 1-butenyl, etc.

The term "alkenyl," as used herein either alone or as part of another group, refers to a substituted or unsubstituted aliphatic hydrocarbon chain that may be straight-chain or branched and contains one or more carbon-carbon double bonds. The one or more double bonds may be internal (such as in 2-butene) or terminal (such as in 1-butene). Preferably alkenyl moieties contain one or two double bonds. The term "alkenyl" includes both E and Z isomers of each of the one or more double bonds. Specifically included within the definition of "alkenyl" are those aliphatic hydrocarbon chains that are optionally substituted. Examples of alkenyl moieties include vinyl, allyl, and butenyl (e.g., 1-butene and 2-butene).

The term "alkenyl," as used herein either alone or as part of another group, refers to a substituted or unsubstituted aliphatic hydrocarbon chain that may be straight-chain or branched and contains one or more triple carbon-carbon bonds. The one or more triple carbon-carbon bonds may be internal (such as in 2-butyne) or terminal (such as in 1-butyne). Specifically included within the definition of "alkenyl" are those aliphatic hydrocarbon chains that are optionally substituted. Examples of alkenyl groups include ethynyl, propynyl, butynyl, pentynyl, and the like.

As used herein either alone or as part of another group, the term "cycloalkyl" refers to substituted or unsubstituted non-aromatic carbocyclic groups including cyclized alkyl, alkenyl, and alkenyl groups. Cycloalkyl groups can be monocyclic (e.g., cyclohexyl) or poly-cyclic (e.g. fused, bridged, or spiro ring systems), wherein the carbon atoms are located inside or outside of the ring system. Any suitable ring position of the cycloalkyl moiety may be covalently linked to the defined chemical structure. Examples of cycloalkyl groups include cyclopropyl, cyclopropylmethyl, cyclobutyl, cyclopentyl, cyclohexyl, cyclohexylmethyl, cyclohexylethyl, cycloheptyl, cyclopentenyl, cyclohexenyl, cyclohexadienyl, cycloheptatrienyl, norbornyl, norpinyl, norcarnyl, adamantyl, spiro[4.5]decanyl groups, homologs, isomers, and the like. Also included in the definition of cycloalkyl groups are moieties that have one or more aromatic rings fused (i.e., having a bond in common with) to the cycloalkyl ring, for example, benzo derivatives of cyclopentane (indanyl), cyclohexane (tetrahydronaphthyl), and the like. Specifically included within the definition of "cycloalkyl" are those carbocycles that are optionally substituted.

As used herein, "cycloheteroalkyl" refers to a substituted or unsubstituted non-aromatic cycloalkyl group that contains at least one ring heteroatom selected from oxygen (O), nitrogen (N) and sulfur (S), and optionally contains one or more double or triple bonds. One or more N or S atoms in a cycloheteroalkyl ring may be oxidized (e.g., morpholine N-oxide, thiomorpholine S-oxide, thiomorpholine S,S-dioxide). Examples of cycloheteroalkyl groups include morpholine, thiomorpholine, pyran, imidazolidine, imidazoline, oxazolidine, pyrazolidine, pyrazoline, pyrrolidine, pyrroline, tetrahydrofuran, tetrahydrothiophene, piperidine, piperazine, and the like. Also included in the definition of cycloheteroalkyl are moieties that have one or more aromatic rings fused (i.e., have a bond in common with) to the cycloheteroalkyl ring, for example, benzimidazoline, chromane, chromene, indolinetetrahydroquinoline, and the like. Cycloheteroalkyl groups may also contain one or more oxo groups, such as phthalimide, piperidone, oxazolidinone, pyrimidine-2,4(1H,3H)-dione, pyridin-2(1H)-one, and the like. Specifically included within the definition of "cycloheteroalkyl" are those ring systems that are optionally substituted on any heteroatom and/or carbon atom that results in a stable structure.

The term "aryl," as used herein either alone or as part of another group, refers to substituted or unsubstituted aromatic monocyclic or polycyclic hydrocarbons such as, for example, phenyl, naphthyl, anthracenyl, phenanthrenyl, pyrenyl, and the like. In some embodiments, aryl groups have from 6 to about 20 carbon atoms. Preferred aryl groups are $C_{6-16}$ aryl and more preferably $C_6$ aryl (i.e., phenyl). Any suitable ring position of the aryl moiety may be covalently linked to the defined chemical structure (e.g., 1-naphthyl, 2-naphthyl, etc.). Specifically included within the definition of "aryl" are those aromatic hydrocarbons that are optionally substituted.

The term "aralkyl" refers to aryl C(1-22)alkyl, and the term "aryl" throughout this specification means phenyl or naphthyl.

The term "aralkyl" refers to an aryl moiety, as defined herein, bonded to an alkyl moiety, as defined herein. Aralkyl groups are covalently linked to the defined chemical structure through their alkyl groups.

Aralkyl groups optionally may be substituted on the aryl moiety, the alkyl moiety, or both. Examples of aralkyl include benzyl and alkylpyrenyl (e.g., methylpyrenyl).

As used herein, "heteroaryl" or "heteroaromatic" refers to monocyclic or polycyclic aromatic ring systems having from 5 to 20 ring atoms and containing 1-4 ring heteroatoms independently selected from O, N and S. Generally, heteroaryl rings do not contain O—O, S—S, or S—O bonds. Heteroaryl groups include monocyclic heteroaryl rings fused to a phenyl ring. The heteroaryl group may be attached to the defined chemical structure at any heteroatom or carbon atom that results in a stable structure. One or more N or S atoms in a heteroaryl ring may be oxidized (e.g., pyridine N-oxide, thiophene S-oxide, thiophene S,S-dioxide). Examples of heteroaryl groups include, for example, pyrrole, furan, thiophene, pyridine, pyrimidine, pyridazine, pyrazine, triazole, pyrazole, imidazole, isothiazole, thiazole, thiadiazole, isoxazole, oxazole, oxadiazole, indole, isoindole, benzofuran, benzothiophene, quinoline, 2-methylquinoline, isoquinoline, quinoxaline, quinazoline, benzotriazole, benztetrazole, indazole, benzimidazole, benzothiazole, benzisothiazole, benzisoxazole, benzoxadiazole, benzoxazole, cinnoline, 1H-indazole, 2H-indazole, indolizin, isobenzofuran, naphthyridine, phthalazine, pteridine, purine, oxazolopyridine, thiazolopyridine, imidazopyridine, furopyridine, thienopyridine, pyridopyrimidine, pyridopyrazine, pyridopyridazine, thienothiazole, thienoxazole, and thienoimidazole. Specifically included within the definition of "heteroaryl" are those aromatic ring systems that are optionally substituted on any heteroatom and/or carbon atom that results in a stable structure.

The phrase "polycyclic group" refers to a fused ring system containing two or more aromatic or aliphatic rings. Each aromatic ring can be an aryl or heteroaryl group as defined herein, and each aliphatic ring can be a cycloalkyl or cycloheteroalkyl group as defined herein. Preferred polycyclic groups are $C_{9-16}$ polycyclic groups. Specifically included within the definition of "polycyclic group" are those ring systems that are optionally substituted on any heteroatom and/or carbon atom that results in a stable structure. Preferred polycyclic groups include optionally substituted fluorene, pyrene, coumarin (i.e., 2H-chromen-2-one), isocoumarin or acridine groups. Examples of polycyclic groups include hydroxycoumarinalkylcarbonyl, fluorenylalkoxycarbonyl, acridinyl carbonyl and pyrene carbonyl, e.g. a 7-hydroxycoumarin-4-methylcarbonyl, 9-fluorenylmethoxycarbonyl, acridine-9-carbonyl and pyrenyl-1-carbonyl group.

By the phrase "hydrophobic group" is meant an optionally substituted aliphatic group, such as an alkyl or alkenyl group, or an optionally substituted aromatic group which comprises an aromatic carbon or heteroaromatic ring system. Preferably, the aromatic group has a $C_5$ to $C_{16}$ aromatic carbon ring or a heteroaromatic ring in which one, two, three or four of the ring carbon atoms are replaced by a multivalent ring heteroatom, for example, nitrogen, phosphorus, silicon, oxygen, or sulphur, though more commonly nitrogen, oxygen, or sulphur. Preferably, the heterocyclic ring has from 1 to 4 heteroatoms, or 1 to 6 heteroatoms for bicyclic groups, and more preferably one or two heteroatoms. The aromatic or heteroaromatic group may be a monocyclic group or a polycyclic group, for example in which two, three or four rings are fused together. Examples of aromatic groups include optionally substituted benzyl, phenyl, naphthalenyl, anthracenyl, fluorenyl or pyrenyl groups, and more preferably a nitrophenyl group or a pyrenylmethyl group. Examples of heteroaromatic groups include optionally substituted furanyl, pyrrolyl, thiophenyl, pyridinyl, quinolinyl, coumarinyl, isoquinolinyl and acridinyl groups, and more preferably an optionally substituted coumarinyl or quinolinyl group. Examples of heteroaromatic groups having monocyclic 5 and 6 membered rings containing 1 to 4 heteroatoms include pyrrolyl, furyl, pyrazolyl, imidazolyl, oxazolyl, isoxazolyl, thiazolyl, isothiazolyl, oxadiazolyl, thiadiazolyl, triazolyl, thiatriazolyl and pyridyl. Examples of heteroaromatic groups based on bicyclic or polycyclic ring systems containing 1 to 6 heteroatoms include quinolinyl, coumarinyl group or acridinyl groups. The aromatic and heteroaromatic groups may be optionally substituted by an alkyl group, thereby forming aralkyl groups, e.g. an alkylpyrenyl group.

By the phrase "hydrophobic group" is meant an optionally substituted aliphatic group, such as an alkyl or alkenyl group; an optionally substituted aryl or heteroaromatic ring system; or an aralkyl group, each defined as described herein. Illustrative hydrophobic groups include benzyl, phenyl, napthyl and pyrenyl.

By the phrase "optionally substituted", in relation to a hydrophobic group or more generally, is meant substitution of the parent group with at least one substituent selected from lower alkyl, alkoxy, hydroxyl, carboxy, amine, thiol, hydrazide, amide, halide, hydroxyl, ether, amine, nitrile, imine, nitro, sulfide, sulfoxide, sulfone, thiol, aldehyde, keto, carboxy, ester, an amide group; including seleno and thio derivatives thereof. Also included in the definition of "optionally substituted" are sulfide, sulfoxide, sulfone and thiol derivates with or without a seleno group. In embodiments in which the aromatic carbon or heteroaromatic ring is substituted such substitutions will typically number less than about 10 substitutions, more preferably about 1 to 5 of same with about 1 or 2 substitutions being preferred for many invention applications. Preferred alkoxy groups include methoxy, ethoxy, and propoxy. Illustrative hydrophobic groups include unsubstituted benzyl, phenyl, and napthyl.

The term "optionally substituted" as used herein means one or more hydrogen atoms (e.g., 1, 2, 3, 4, 5, or 6 hydrogen atoms) of the group may each be replaced with a substituent atom or group commonly used in pharmaceutical chemistry. Each substituent may be the same or different. Examples of suitable substituents include, but are not limited to, alkyl, alkenyl, alkenyl, cycloalkyl, aryl, aralkyl, cycloheteroalkyl, heteroaryl, alkoxy (e.g., methoxy, ethoxy, and propoxy), aryloxy, heteroaryloxy, aralkyloxy, hydroxyalkyl, alkylthio, alkoxycarbonyl, alkoxyalkoxy, perfluoroalkyl, perfluoroalkoxy, alkoxyalkyl, hydroxyl, carboxy, amine, thiol, hydrazide, amide, halide, ether, nitrile, imine, nitro, sulfide, sulfoxide, sulfone, sulfonamide, thiol, aldehyde, keto, carboxylic acid, and ester, including seleno and thio derivatives thereof. In embodiments in which a functional group with an aromatic carbon ring is substituted, such substitutions will typically number less than about 10 substitutions, more preferably about 1 to 5, with about 1 or 2 substitutions being preferred.

The carbon numbers used in the definitions herein (e.g., $C_{1-6}$ alkyl, $C_{2-6}$alkenyl, $C_{2-6}$alkenyl, $C_{6-10}$aryl, etc.) refer to the carbon backbone and carbon branching, but do not include carbon atoms of substituents.

At various places in the present specification substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl.

The compounds of the invention can contain an asymmetric atom (also referred as a chiral center), and some of the compounds can contain one or more asymmetric atoms or centers, which can thus give rise to optical isomers enantiomers and diastereomers. The invention includes such optical isomers enantiomers and diastereomers, as well as the racemic and resolved, pure R and S stereoisomers, as well as other mixtures of the R and S stereoisomers and pharmaceutically acceptable salts thereof. Optical isomers can be obtained in pure form by standard procedures known to those skilled in the art, which include, but are not limited to, diastereomeric salt formation, kinetic resolution, and asymmetric synthesis.

The invention also encompasses cis and trans isomers of compounds containing alkenyl moieties (e.g., alkenes and imines). It is also understood that the invention encompasses all possible regioisomers, and mixtures thereof, which can be obtained in pure form by standard separation procedures known to those skilled in the art, and include, but are not limited to, column chromatography, thin-layer chromatography, and high-performance liquid chromatography.

Pharmaceutically acceptable salts of the compounds of the invention having an acidic moiety can be formed using organic and inorganic bases. Suitable salts formed with bases include metal salts, such as alkali metal or alkaline earth metal salts, for example sodium, potassium, or magnesium salts; ammonia salts and organic amine salts, such as those formed with morpholine, thiomorpholine, piperidine, pyrrolidine, a mono-, di- or tri-lower alkylamine (e.g., ethyl-tert-butyl-, diethyl-, diisopropyl-, triethyl-, tributyl- or dimethylpropylamine), or a mono-, di- or trihydroxy lower alkylamine (e.g., mono-, di- or triethanolamine). Internal salts also may be formed. Similarly, when a compound of the present invention contains a basic moiety, salts can be formed using organic and inorganic acids. For example, salts can be formed from the following acids: acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, and camphorsulfonic as well as other known pharmaceutically acceptable acids. Amino acid addition salts can also be formed with amino acids such as lysine, glycine, or phenylalanine.

In a further aspect, the present invention provides derivatives of the compounds, and more particularly protected forms of the compounds. By way of example, the compounds may be protected at their N- and/or C-termini, and/or at the amino acid side chain (in those compounds wherein $R^1$ is an amino acid side chain). Examples of protecting groups include tBu, Boc, Fmoc, Fm, Benzyl, Dde and Z and also include the compounds when coupled to a solid phase, e.g. when they have been made by solid phase synthesis.

The terms "intercellular communication modulator", "gap junction facilitator", "compound that facilitates gap junction communication" and "gap junction opener", etc., all refer to a compound that facilitates, or maintains, or normalizes, GJIC, irrespective of the particular mechanism behind this action. More specifically, the term "gap junction opener" may refer to a substance which normalizes (i.e., increases) the exchange of molecules that are able to pass through gap junctions between extracellular and intracellular spaces and/or which can normalize increase GJIC.

The term "agonist" refers to a compound that can interact with a tissue, cell or cell fraction which is the target of an AAP, AAP10, HP5 compound, or functional analogue thereof, to cause substantially the same physiological responses in the tissue, cell or cell fraction as the AAP, AAP10, HP5 compound, or functional analogue thereof. In one aspect, the physiological response is one or more of: contraction, relaxation, secretion, enzyme activation, etc. Preferably, the compound binds to the tissue, cell or cell fraction. In one aspect, the compound binds to a receptor on the tissue, cell, or cell fraction, which binds to AAP, AAP10, HP5, or a functional analogue thereof.

An "antiarrhythmic compound agonist" as used herein is a compound, which comprises an antiarrhythmic activity, which is substantially the same, or greater than, the antiarrhythmic activity of an AAP, AAP10, HP5 compound or functional analogue thereof. "Greater than" refers to an antiarrhythmic activity, which is observed at lower concentrations of compound or in shorter periods of time compared to the antiarrhythmic activity of an AAP, AAP10, HP5 compound or functional analogue thereof.

The term "antagonist" refers to a compound which inhibits or antagonizes one or more physiological responses observed in a tissue, cell or cell fraction after contacting the tissue, cell, or cell fraction with AAP, AAP10, HP5 compound, or a functional analogue thereof. In one aspect, the physiological response is one or more of: contraction, relaxation, secretion, enzyme activation, etc. Preferably, the compound binds to the tissue, cell or cell fraction. In one aspect, the compound binds to a receptor on the tissue, cell, or cell fraction which binds to AAP, AAP10, HP5, or a functional analogue thereof and/or which inhibits binding of one or more of AAP, AAP10, HP5, a functional analogue thereof, to the receptor.

As used herein, "normalize" refers to a change in a physiological response such that the response becomes insignificantly different from one observed in a normal patient. Thus, normalization may involve an increase or decrease in the response depending on the pathology involved.

The "IC50" of a compound according to the invention refers to the concentration of a compound that is required for 50% inhibition of a response or activity mediated by an antiarrhythmic compound such as AAP, AAP10, HP5 or a functional analogue thereof. In one aspect, a compound which is an antagonist of AAP, AAP10, HP5 or a functional analogue thereof, is a compound which has an IC50 of less than about $10^{-6}$ M, and preferably, less than about $10^{-8}$ M.

The "EC50" of a compound according to the invention refers to the plasma concentration/AUC of compound required for obtaining 50% of a maximum effect observed for an AAP, AAP10, HP5 compound or a functional analogue thereof. In one aspect, a compound which is an agonist of AAP, AAP10, HP5 or a functional analogue thereof, is a compound which has an EC50 of less than about $10^{-6}$ M, and preferably, less than about, $10^{-8}$ M.

It has been shown that the antiarrhythmic property of peptide compounds, such as AAP and the peptides disclosed in WO 01/62775 is related to an ability of modulating or enhancing gap junction intercellular communication (GJIC) especially of cardiac cells. Thus, it may be assumed the present N- or C-terminally modified small peptide compounds also have a wide spectrum of useful applications including use in the treatment or prevention of pathologies associated with impaired GJIC.

In one aspect, the present invention relates to an N- or C-terminally modified peptide represented by Formula I:

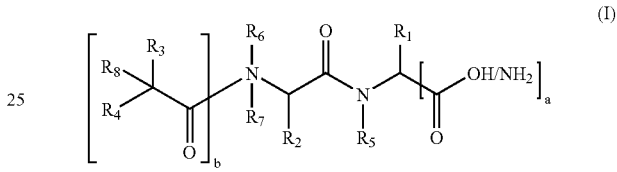

(I)

wherein:

a and b independently is 0 or 1, and if a is 0 then b is 1 or if a is 1 then b is 0, and wherein $R_2$ is any amino acid side chain, preferably Gly, Ala, Leu, Val, Ile, Nle, Nva, Lys, Orn, Dab, Dapa, Arg, Asn, Gln, Asp, Glu, Tyr, His, Trp or Phe; and $R_5$ is H or Me with the proviso that when a is 1 then $R_1$ is any amino acid side chain, preferably Tyr, Phe, His, Trp, Nal, Gly, Ala, Leu, Val, Ile, Nle, Nva, Asp, Asn, Glu or Gln; and when a is 0 then $R_1$ is an optionally substituted aromatic group which comprises an aromatic carbon or heteroaromatic ring system; and when b is 0 then $R_7$ is H or Me; and $R_6$ is an arylcarbonyl, aryloxycarbonyl, arylalkoxycarbonyl, polycyclic carbonyl, polycyclic oxycarbonyl or polycyclic alkoxycarbonyl group, optionally substituted with one or more substituents as defined herein; and when b is 1 then $R_3$ is H, $NH_2$, OH, SH, RO, RS, RSO, $RSO_2$, COR, CSR, COOH, COOR, $CONH_2$, CONHR, $CON(R)_2$, OCOR, SCOR, or an optionally substituted phenyl or benzyl group, and $R_4$ is H, or any amino acid side chain, preferably Ala, Ser, Thr, Leu, Ile, Val, Met, Nle or Nva, and $R_6$ is H or Me, and $R_7$ is missing, and $R_8$ is H, alkyl, cycloalkyl, aryl or aralkyl; or a pharmaceutically acceptable salt thereof.

When b is 0 then $R_6$ is an arylcarbonyl, aryloxycarbonyl, arylalkoxycarbonyl, polycyclic carbonyl, polycyclic oxycarbonyl or polycyclic alkoxycarbonyl group, optionally substituted with one or more substituents as defined herein.

Preferred aryl groups include benzyl groups and the most preferred group is benzoyl, i.e. providing a benzylcarbonyl group.

Preferred polycyclic groups include an optionally substituted pyrene, coumarin or acridine group. More preferred examples of polycyclic groups include a hydroxycoumarinalkylcarbonyl, fluorenylalkoxycarbonyl, acridinyl carbonyl or pyrene carbonyl group, e.g. a 7-hydroxycoumarin-4-methylcarbonyl, 9-fluorenylmethoxycarbonyl, acridine-9-carbonyl or pyrenyl-1-carbonyl group.

Preferred polycyclic groups are $C_{9-16}$ polycyclic groups. Preferred alkyl or alkoxy groups are $C_{1-10}$ alkyl and more preferably $C_{1-5}$ alkyl. Preferred aryl groups are $C_{5-8}$ aryl and more preferably $C_{5-6}$ aryl.

Preferred hydrophobic groups are set out in the definition provided above and include optionally substituted aromatic groups which comprise an aromatic carbon or heteroaromatic ring system which may be monocyclic or a polycyclic aromatic compound, such as a pyrene or fluorene. The compounds may include a free N-terminal, or a free C-terminal, or both. Compounds within the scope of the present invention are often represented herein with free N-terminal and/or C-terminal group. These groups may remain free for some invention uses. However, in another embodiment, the compounds can feature blocked C-terminal groups and free N-groups. Alternatively, such compounds may have blocked N-groups and free C-terminal groups, or blocked N- and C-terminal groups.

In another embodiment of the invention "[ ]a" in formula I is absent. This leads to the following compound having the general formula II:

(II)

wherein:

$R_2$ is any amino acid side chain, preferably Gly, Ala, Leu, Val, Ile, Nle, Nva, Lys, Orn, Dab, Dapa, Arg, Asn, Gln, Asp, Glu, Tyr, His, Trp or Phe; and $R_5$ is H or Me; and $R_1$ is an optionally substituted aromatic group which comprises an aromatic carbon or heteroaromatic ring system; and $R_3$ is H, $NH_2$, OH, SH, RO, RS, RSO, $RSO_2$, COR, CSR, COOH, COOR, $CONH_2$, CONHR, $CON(R)_2$, OCOR, SCOR, or an optionally substituted phenyl group or benzyl, wherein R is an optionally substituted alkyl, alkenyl, alkenyl, aryl, aralkyl or cycloalkyl group; and $R_4$ is H, or any amino acid side chain, preferably Ala, Ser, Thr, Leu, Ile, Val, Met, Nle or Nva; and $R_6$ is H or Me; and $R_8$ is H, alkyl, cycloalkyl, aryl or aralkyl;

or a pharmaceutically acceptable salt thereof.

In a further embodiment of the invention "[ ]b" in formula (I) is missing and the compound has the following general formula III:

(III)

wherein:

$R_2$ is any amino acid side chain, preferably Gly, Ala, Leu, Val, Ile, Nle, Nva, Lys, Orn, Dab, Dapa, Arg, Asn, Gln, Asp, Glu, Tyr, His, Trp or Phe; and $R_5$ is H or Me;

$R_1$ is any amino acid side chain, preferably Tyr, Phe, His, Trp, Nal, Gly, Ala, Leu, Val, Ile, Nle, Nva, Asp, Asn, Glu or Gln; and $R_7$ is H or Me;

and $R_6$ is an arylcarbonyl, aryloxycarbonyl, arylalkoxycarbonyl, polycyclic carbonyl, polycyclic oxycarbonyl or polycyclic alkoxycarbonyl group, optionally substituted with one or more substituents as defined herein; or a pharmaceutically acceptable salt thereof.

Preferred aryl groups include benzyl groups and the most preferred group is benzoyl, i.e. providing a benzylcarbonyl group.

Preferred polycyclic groups include an optionally substituted pyrene, coumarin or acridine group. More preferred examples of polycyclic groups include a hydroxycoumarinalkylcarbonyl, fluorenylalkoxycarbonyl, acridine carbonyl or pyrene carbonyl group, e.g. a 7-hydroxycoumarin-4-methylcarbonyl, 9 fluorenylmethoxycarbonyl, acridine-9-carbonyl or pyrenyl-1-carbonyl group.

Preferred polycyclic groups are $C_{9-16}$ polycyclic groups. Preferred alkyl or alkoxy groups are $C_{1-10}$ alkyl and more preferably $C_{1-5}$ alkyl. Preferred aryl groups are $C_{5-8}$ aryl and more preferably $C_{5-6}$ aryl.

In formula I when a=1 and b=0 and in formula III, preferred $R_2$ amino acid side chains are Asn, Gly or Gln, and more preferably Asn and Gly. Preferred $R_1$ amino acid side chains are Gly, Tyr, Asn or D-Asn, and more preferably Tyr and Gly. Preferred combinations of $R_2$ and $R_1$ amino acid side chains include Asn-Gly and Asn-Tyr.

In formula I when b=1 and a=0 and in formula II, a preferred $R_4$ amino acid side chain is Gly and a preferred $R_2$ amino acid side chain is Asn and a preferred combination of $R_4$ and $R_2$ side chains is Gly-Asn.

In one aspect, the present invention relates to an N- or C-terminally modified peptide represented by formula IV:

(IV)

or a pharmaceutically acceptable salt thereof, wherein:
a is 0 or 1;
$R^1$ is hydrogen or an amino acid side chain;
$R^2$ is an amino acid side chain;
$R^3$ is selected from the group consisting of $OR^8$, $N(R^8)_2$, optionally substituted aryl, optionally substituted heteroaryl, and an optionally substituted polycyclic group;

R⁵ is H or $C_{1-6}$ alkyl;
R⁷ is H or $C_{1-6}$ alkyl;
R⁸, at each occurrence, independently is selected from the group consisting of H, $C_{1-6}$alkyl, and $C(O)C_{1-6}$ alkyl;
X is O or S; and
Y is selected from the group consisting of $C(O)OR^8$, $C(O)N(R^8)_2$, optionally substituted aryl, optionally substituted heteroaryl, and an optionally substituted polycyclic group; provided that:

when Y is $C(O)OR^8$ or $C(O)N(R^8)_2$, then a is 1 and R¹ is an amino acid side chain;

when a is 1, Y is $C(O)NH_2$, R¹ is the side chain of Tyr, X is O, and R³ is $N(R^8)_2$, then R⁸ is not acetyl, hydroxyacetyl or thiohydroxyacetyl; and when a is 0, Y is substituted aryl, X is O, and R³ is $N(R^8)_2$, then R⁸ is not acetyl, hydroxyacetyl or thiohydroxyacetyl.

In formula IV, $R_7$ may be an alkylcarbonyl or alkoxyalkylcarbonyl. Preferred alkylcarbonyl groups include an acetyl or diacetyl group, optionally substituted with one or more hydroxyl, alkoxy or thiohydroxy groups, e.g. providing a hydroxyacetyl, thiohydroxyacetyl, methoxyacetyl or acetyl (hydroxy)acetyl group.

A compound of formula IV may have the structure of formula V:

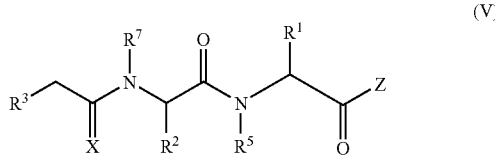

(V)

or a pharmaceutically acceptable salt thereof, wherein
R¹, R², R³, R⁵, R⁷, R⁸ and X are defined as described for formula IV; and
Z is $OR^8$ or $N(R^8)_2$;

provided that when Y is $NH_2$, R¹ is the side chain of Tyr, X is O, and R³ is $N(R^8)_2$, then R⁸ is not acetyl, hydroxyacetyl or thiohydroxyacetyl.

A compound of formula IV may have the structure of formula VI:

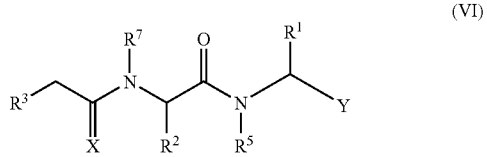

(VI)

or a pharmaceutically acceptable salt thereof, wherein
R², R³, R⁵, R⁷, R⁸ and X are defined as described for formula IV;
R¹ is H; and
Y is aryl, heteroaryl, or a polycyclic group.

A compound of formula IV may have the structure of formula VII:

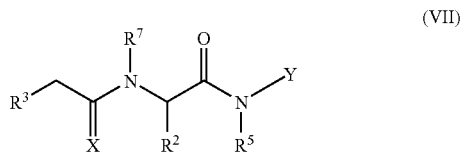

(VII)

or a pharmaceutically acceptable salt thereof, wherein
R², R³, R⁵, R⁷, R⁸ and X are defined as described for formula IV; and
Y is aryl, heteroaryl, or a polycyclic group;

provided that when Y is substituted aryl, X is O, and R³ is $N(R^8)_2$, then R⁸ is not acetyl, hydroxyacetyl or thiohydroxyacetyl.

More specific compounds within the scope of the invention are shown in Table 1 below.

TABLE 1

| Compound No. | Compound Name |
|---|---|
| 1 | N-(7-hydroxycoumarin-4-acetyl)-Asn-Gly-NH₂ |
| 2 | N-(hydroxyacetyl)-Gly-Tyr-NH₂ |
| 3 | N-(hydroxyacetyl)-Gln-Tyr-NH₂ |
| 4 | N-(9-fluorenylmethyloxycarbonyl)-Asn-Gly-NH₂ |
| 5 | N-(acridin-9-carbonyl)-Asn-Gly-NH₂ |
| 6 | N-(pyrenyl-1-carbonyl)-Asn-Tyr-NH₂ |
| 7 | N-(thiohydroxyacteyl)-Asn-Tyr-NH₂ |
| 8 | N-((acetylhydroxy)acetyl))-Asn-Tyr-NH₂ |
| 9 | H-Gly-Asn-NH(4-methyl-coumarin-7-yl) |
| 10 | H-Gly-Asn-NH(4-nitrophenyl) |
| 11 | Ac-Gly-Asn-NH(4-nitrophenyl) |
| 12 | H-Gly-Asn-NH(pyrenylmethyl) |
| 13 | Ac-Gly-Asn-NH(pyrenylmethyl) |
| 14 | Ac-Gly-Asn-NH(quinolin-6-yl) |
| 15 | N-(7-hydroxycoumarin-4-acetyl)-D-Asn-Gly-OH |
| 16 | (Methoxyacetyl)-Asn-Tyr-NH₂ |

| Compound No. | IUPAC Name |
|---|---|
| 1 | (S)-N*1*-Carbamoylmethyl-2-[2-(7-hydroxy-2-oxo-2H-chromen-4-yl)-acetylamino]-succinamide |
| 2 | (S)-2-[2-(2-Hydroxy-acetylamino)-acetylamino]-3-(4-hydroxy-phenyl)-propionamide |
| 3 | (S)-2-(2-Hydroxy-acetylamino)-pentanedioic acid 5-amide 1-{[(S)-1-carbamoyl-2-(4-hydroxy-phenyl)-ethyl]-amide} |
| 4 | [(S)-2-Carbamoyl-1-(carbamoylmethyl-carbamoyl)-ethyl]-carbamic acid 9H-fluoren-9-ylmethyl ester |
| 5 | (S)-2-[(Acridine-9-carbonyl)-amino]-N*1*-carbamoyl-methyl-succinamide |
| 6 | (S)-N*1*-Carbamoylmethyl-2-[(9,10b-dihydro-pyrene-1-carbonyl)-mino]-succinamide |
| 7 | (S)-N*1*-[(S)-1-Carbamoyl-2-(4-hydroxy-phenyl)-ethyl]-2-(2-mercaptoacetylamino)-succinamide |
| 8 | Acetic acid {(S)-2-carbamoyl-1-[(S)-1-carbamoyl-2-(4-hydroxy-phenyl)-ethylcarbamoyl]-ethylcarbamoyl}-methyl ester |
| 9 | (S)-2-(2-Amino-acetylamino)-N*1*-(4-methyl-2-oxo-2H-chromen-7-yl)-succinamide |
| 10 | 2-(2-Amino-acetylamino)-N*1*-(4-nitro-phenyl)-succinamide |
| 11 | (S)-2-(2-Acetylamino-acetylamino)-N*1*-(4-nitro-phenyl)-succinamide |
| 12 | (S)-2-(2-Amino-acetylamino)-N*1*-pyren-1-ylmethyl-succinamide |
| 13 | (S)-2-(2-Acetylamino-acetylamino)-N*1*-pyren-1-ylmethyl-succinamide |
| 14 | (S)-2-(2-Acetylamino-acetylamino)-N*1*-quinolin-6-yl-succinamide |
| 15 | {(R)-3-Carbamoyl-2-[2-(7-hydroxy-2-oxo-2H-chromen-4-yl)-acetylamino]-propionylamino}-acetic acid |
| 16 | (S)-N*1*-[(S)-1-Carbamoyl-2-(4-hydroxy-phenyl)-ethyl]-2-(2-methoxy-acetylamino)-succinamide |

Therapeutic compounds of the invention are suitably administered in a protonated and water-soluble form, e.g., as a pharmaceutically acceptable salt, typically an acid addition salt such as an inorganic acid addition salt, e.g., a hydrochloride, sulfate, or phosphate salt, or as an organic acid addition salt such as an acetate, maleate, fumarate, tartrate, or citrate salt. Pharmaceutically acceptable salts of therapeutic compounds of the invention also include metal salts, particularly alkali metal salts such as a sodium salt or potassium salt; alkaline earth metal salts such as a magnesium or calcium salt; ammonium salts such an ammonium or tetramethyl ammonium salt; or an amino acid addition salts such as a lysine, glycine, or phenylalanine salt.

Antiarrhythmic Peptides

More particular compounds according to the invention may facilitate and/or maintain the intercellular communication mediated by gap junctions. In one aspect, the compounds act as antiarrhythmic peptides (AAPs), which target the same cells targeted by AAP, AAP10, HP5, and/or functional analogues thereof, i.e. the compounds are able to modulate the function of these cells by agonizing or antagonizing the function of AAP, AAP10, HP5, and/or functional analogues thereof. The scope of the present invention is, however, not limited to compound having specific AAP agonistic or antagonistic properties. The invention also relates to the preparation and use of pharmaceutical compositions for the treatment of pathologies which may be associated with impaired intercellular gap junction communication and methods for using these compositions. In a further aspect compounds in accord with the invention show good activity in one or more of the following assays.

Binding Assay

Accordingly, and in one embodiment, additionally preferred compounds show binding, preferably specific binding, to a tissue, cell, or cell fraction in what is referred to herein as a "standard AAP site binding test". The test can detect and optionally quantify binding of a subject compound, e.g., AAP, AAP10, HP5, or a functional analogue thereof. In one preferred embodiment, the invention compound is a modulator of the function of such a tissue, cell, or cell fraction (i.e., the compound agonizes or antagonizes the function of the antiarrhythmic peptide). In another embodiment, the compound is a modulator of a receptor for the antiarrhythmic peptide (i.e., the compound is an agonist or antagonist of the receptor).

Additionally preferred peptides according to Formula I above show good function as a modulator of gap junctional communication (e.g., as agonists or antagonists of AAP). In one aspect, the peptides function as an antiarrhythmic drug.

Cardio-Related Assays

Preferred agonist compounds of the invention provide an intracellular conductance (Gj) that is substantially the same as, or is greater than, the Gj of AAP in what is referred to herein as a "standard cardiomyocyte assay". Preferred antagonist compounds provide a Gj that is less (e.g., at least about 10%, or at least about 20% less) than the Gj of AAP and/or block the ability of AAP to normalize the Gj of an ischemic cell, i.e., to return the Gj to substantially the same values found in non-ischemic cells.

Additionally preferred compounds according to the invention increase the time to an AV block in a mouse after infusion of $CaCl_2$, in what is referred to herein as a "standard calcium-induced arrhythmia assay." Preferably, the compounds provide at least about 50% of the activity of AAP, preferably at least about 70% of the activity of AAP, more preferably substantially the same activity of AAP (i.e., show time lags of approximately the same duration).

Peptides of the invention may additionally show decreases in the incidence of reentry arrhythmias or in the size of an infarct zone observed in what is referred to herein as a "standard ventricular reentry assay." Preferably, the peptides provide at least about 50% of the activity of AAP, preferably at least about 70% of the activity of AAP, more preferably substantially the same activity of AAP in this assay (i.e., providing similar decreases in incidence or infarct zones of similar or smaller size).

Half-Life

Additionally preferred compounds as represented by Formula I, II or III exhibit a good half-life according to what is referred to herein as an "in vitro plasma stability assay" or related phrase. Compounds that show a good stability in the assay have in one embodiment a half-life of more than about 48 hours, such as more than 24 hours, for example more than 12 hours, such as more than 6 hours, for example more than 3 hours, such as more than 1 hour, for example more than 30 minutes, such as more than 20 minutes, for example more than 15 minutes, such as more than 10 minutes, for example more than 5 minutes, such as more than 1 minute. In this embodiment, the compounds of the invention may show enhanced stability in the bloodstream.

Osteoporosis Assay

There is understanding that GJIC is important in bone formation. Preferred compounds of the invention may additionally, or alternatively, show anti-osteoporosis activity, such as an increase in osteoblast activity in what is referred to herein as a "standard osteoblast activity assay" which measures either calcium wave formation and/or alkaline phosphatase activity of osteoblast cells in the presence of the compounds. Preferably, such compounds increased calcium wave activity, manifested as an increase in the number of cells involved in a wave (as determined by measuring levels of intracellular $Ca^{2+}$ using a calcium sensitive fluorescent dye, such as fura-2 and counting the number of cells which fluoresce). Alkaline phosphatase activity also can be used to provide a measure of osteoblast activity using standard colorimetric assays. Compounds according to the invention provide at least about 10% of the activity of AAP in such an assay, such as at least about 20% activity, for example at least about 30% activity, such as at least about 40% activity, for example at least about 50% of the activity of AAP, preferably, at least about 70% activity, and still more preferably, 100% or greater activity of the activity of AAP.

Particular assays useful for identifying and optionally quantifying the activity of preferred compounds of the invention are further described below.

A. Standard Plasma Stability Assays

The invention also provides compounds that have enhanced stability in vitro or in vivo. In another aspect, the compound comprises one or more D-amino acids. In a further aspect, the compound has enhanced stability in a standard stability assay. In one aspect, an in vitro plasma stability assay is performed as described in PCT/US02/05773, filed Feb. 22, 2002. As disclosed in the PCT/US02/05773 application, compounds can be incubated in plasma or serum and samples taken at regular intervals for analysis by HPLC or LC/MS/MS, to quantify the amount of undegraded compound. Appropriate conditions (column, solvent, gradient, and temperature) for such analyses are estimated to ensure that the compound peak and the plasma peaks do not have the same retention time. This is done by subsequent injections of a compound, plasma, and a co-injection with the compound and the plasma, followed by optimization of LC method parameters until a satisfactory separation is obtained. A control plasma sample without the peptide compound, treated in the same manner, also can be taken and evaluated. The samples may include, but are not limited to, a blank, the compound at a suitable concentration (e.g., 0.1 mg/mL), plasma without compound, one or more samples for t=0, and one or more samples at each regular interval. Preferably, multiple samples are taken in parallel. The sample concentrations (peak height in mAU or ion counts) can be plotted vs. time and fitted to a function describing a mono exponential decay (e.g., using a standard Excel package). Preferably, a compound according to the invention has a half-life of more than about 48 hours, such as more than 24 hours, for example more than 12 hours, such as more than 6 hours, for example more than 3 hours, such as more than 1 hour, for example more than 30 minutes as determined using this assay. Plasma stability can be examined in vivo using standard assays. For example, compounds may be administered to a mammal, such as a rat, by bolus injections in volumes of about 1 ml/kg for both i.v. and p.o. dosing. Preferably, compounds are tested in parallel with control samples such as buffer or an antiarrhythmic peptide with a known stability. Blood samples are collected at different time periods (e.g., at B.D. 5, 15, 30, 60, 90, 120, 180, and 240 minutes, where B.D. refers to before dose). Amounts of compounds in samples can be quantified using methods of routine in the art, such as LC/MS/MS. For example, the concentrations of compounds in plasma samples may be calculated from an external standard curve covering concentration ranges of compound from 1.00 to 1000 nM. The plasma concentrations versus time data can be used for pharmacokinetic modelling in WinNonLin 3.5 (Pharsight, Mountain view, Calif.) using non-compartmental analysis and the resulting parameters of AUC, Fpo, Clb, t1/2, Cmax and tmax can be determined as is known in the art.

B. Standard Cardiomyocyte Assays

In one aspect, a compound according to the invention is administered to a cardiac cell and gap junction function is evaluated. Optimal compounds for such procedures can be identified in standard cardiomyce assays. In one aspect, cardiac cells are isolated from a mammal, such as a guinea pig hearts by perfusion with collagenase according to the Langendorf method. The cells are exposed to compound and evaluated for GJIC by patch clamp using methods known in the art. Intercellular conductance (Gj) using the formula:

$$G_j = \frac{\Delta I_p}{\Delta U_j} = \frac{I_{p,pulse} - I_{p,rest}}{U_p - U_a} \quad \text{(Equation 1)}$$

Where Ip,pulse and Ip,rest represent the current in the passive cell during the pulse and before the pulse respectively, and Up and Ua represent the voltage of the passive and active cell. The change in Gj value upon compound administration is analyzed by comparing the relative changes in Gj. For example, the relative Gj as a function of time before, and during, stimulation with compound (e.g., at about $10^{-8}$ M) can be determined. Preferably, the compound provides a Gj, which is substantially the same as the Gj (±10%) of an antiarrhythmic peptide such as AAP, AAP10, HP5, and functional analogues thereof. In one aspect, the cell is an ischemic cell, and the compound provides a Gj, which is substantially the same as that of a non-ischemic cell (±20%, preferably, ±10%). Additional details concerning performing cardiomyocyte assays are provided in PCT/US02/05773, filed Feb. 22, 2002.

C. Standard Calcium-Induced Arrhythmia Assay

Peptides suitable for administration to cardiac cells can be identified in an in vivo model of calcium-induced arrhythmias according to the model of Lynch et al. (1981) *J Cardiovasc. Pharmacol.* 3:49-60. Mice (25-30 g) are anaesthetized with a neurolept anaesthetic combination and an i.v. cannula is inserted into the tail vein. A lead II ECG signal is recorded continuously by positioning a stainless steel ECG electrodes on the right forelimb and on the left hind limb. The ground electrode is placed on the right hind limb. The signal is amplified (×5.000-10.000) and filtered (0.1-150 Hz) via a Hugo Sachs Electronic model 689 ECG module. The analogue signal is digitized via a 12 bit data acquisition board (Data Translation model DT321) and sampled at 1000 Hz using the Notocord HEM 3.1 software for Windows NT. After a 10-minute equilibration period, the test sample of compound is injected into the tail vein. Mice pre-treated with buffer are tested as a measure of the control level in untreated animals. The injection volume is 100 μl in all experiments.

Infusion of $CaCl_2$ (30 mg/ml, 0.1 ml/min≈100 mg/kg/min (calcium chloride-2-hydrate, Riedel-de Haën, Germany)) is started 3 min after i.v. administration of drug or vehicle. The time lag to onset of 2nd degree AV-block is determined as the time from the start of $CaCl_2$ infusion until the first arrhythmic event occurs. An event of 2nd degree AV-block is defined as intermittent failure of the AV conduction characterised by a P-wave without the concomitant QRS complex.

Responses are expressed relative to the time until 2nd degree AV-block occurred in vehicle treated mice. The maximal effect of compounds (e.g., N- or C-terminally modified peptides of the invention, AAP, AAP10 or controls) is determined. Preferably, compounds according to the invention have antiarrhythmic activity comparable to the compounds AAP, AAP10, HP5, or a functional analogue thereof, i.e., the compounds increase the time to an AV block in a mouse after infusion of $CaCl_2$. Preferably, the compounds provide at least about 40% of the activity of AAP, for example at least about 50% of the activity of AAP, such as about 60% of the activity of AAP, for example at least about 70% of the activity of AAP, such as at least about 80% of the activity of AAP, for example at least about 90% of the activity of AAP, for example at least about substantially the same activity of AAP, such as about 110% of the activity of AAP, for example at least about 120% of the activity of AAP, such as at least about 130% of the activity of AAP, for example at least about 140% of the activity of AAP, such as about 150% of the activity of AAP, for example at least about 160% of the activity of AAP, such as at least about 170% of the activity of AAP, for example at least about 180% of the activity of AAP, preferably at least about 190% of the activity of AAP, more preferably at least about 200 or greater % of the activity of AAP (i.e., the compounds show time lags of approximately the same duration as induced by AAP).

D. Standard Osteoblast Activity Assay

Modulation of intercellular communication represents a mechanism by which osteotropic factors regulate the activity of bone forming cells. Therefore, in one aspect, compounds according to the invention may be used to increase osteoblast activity thereby enhancing bone formation in vivo. Without being bound to any specific mechanism of action, it is, however, thought that said increased osteoblast activity is due to increasing gap junctional communication between bone cells. The efficacy of a compound according to the invention may be assayed in preliminarily in human osteoblast cells (hOB), for example by measuring calcium wave activity and/or alkaline phosphatase activity. In one aspect, cells are isolated from human bone marrow obtained by puncture of the posterior iliac spine of healthy volunteers (aged 20-36): 10-15 ml marrow material was collected in 15 ml PBS+Ca,Mg (Life Technologies, Cat. No. 14040) with 100 U/ml Heparin (Sigma, Cat. No. H-3149). The mononuclear fraction of the marrow is isolated on a Lymphoprep gradient (Nycomed Pharma, Cat. No. 1001967), by centrifugation at 2200 rpm for 30 min. After harvesting, the mononuclear fraction is washed once with culture medium and centrifuged at 1800 rpm for 10 min. Subsequently cells are counted and plated in culture medium at $5 \times 10^6$ cells/100 mm dish. hOB medium (all reagents obtained from Life Technologies): MEM w/o Phenol Red w/Glutamax (Cat. No. 041-93013) supplemented with 10% heat inactivated fetal calf serum (Cat. No. 10106) and 0.1% Penicillin/Streptomycin (Cat. No. 15140). Medium is changed the following day and the cells are cultured at 37° C. in 5% $CO_2$ with medium change every 7 days. After 4-6 weeks of culture, the cells will reach 70% confluence. The medium is then supplemented with 100 nM Dexamethasone (Sigma, Cat. No. D-4902) for 7 days. Cells are then plated for video imaging experiments: a 25 mm #1 glass cover slip is placed in a 35 mm dish (or each well of a 6-well multi-dish), cells are plated at $2.5 \times 10^5$ cells/cover slip and cultured for 2-3 days before use.

ROS 17/2.8 cells are cultured in 100 mm dishes at 37° C. with 5% $CO_2$ and medium changed every 2-3 days. ROS medium (all reagents obtained from Life Technologies): MEM (Cat. No. 31095) is supplemented with 10% heat-inactivated calf serum (Cat. No. 16170), 1% NEAA (Cat. No. 11140), 1% Sodium Pyruvate (Cat. No. 11360), 1% L-Glutamine (Cat. No. 25030) and 0.1%
Penicillin/Streptomycin (Cat. No. 15140). For video imaging experiments, cells are plated on cover slips at $2-3\times10^5$ cells/cover slip and cultured for 2-3 days before use.

The cells cultured on cover slips are loaded with 5 μM fura-2-AM (Molecular Probes, Cat. No. F-1221), for 30 minutes at 37° C., and incubated in fresh medium for 20 minutes. Cover slips are then affixed to a PDMI-2 culture chamber (Medical Systems Corp.), maintained at 37° C. with superfused $CO_2$, on a Zeiss Axiovert microscope. Intercellular calcium waves are induced by mechanical stimulation of a single cell using a borosilicate glass micropipette affixed to an Eppendorf 5171 micromanipulator.

Imaging is performed using a MetaMorph imaging system (Universal Imaging). The excitation light (340 and 380 nm) is provided by a monochromator (T.I.L.L. Photonics GmbH). Images are acquired with an intensified CCD camera (Dage MTI) and digitized with a Matrox MVP image processing board. The number of cells involved in a calcium wave in the presence and absence of compound can be used to provide a measure of increase in GJIC.

Cells also can be measured for the presence of alkaline phosphatase activity to provide a general measure of osteoblast activity. In one aspect, cells are plated in 96-well plates at a concentration of 8000 cells/well (hOB) or 3000 cells/well (ROS) in 200 μl normal culture medium. On day 4 (or day 3 for ROS cells), cells are washed with 200 μl MEM, 0.1% BSA (Sigma, Cat. No. A-9418). Samples comprising a suitable medium (e.g., 200 μl MEM, 0.1% BSA) containing various concentrations of compounds, control, AAP or AAP10 are added to the cells, and culture is continued for about 4 days (2 days for ROS cells).

On about day 8 (preferably day 5 for ROS cells), cells are assayed for alkaline phosphatase using an Alkaline Phosphatase (ALP) assay such as is known in the art. ALP assays are generally colorimetric endpoint methods for measuring enzyme activity, and can be performed using an Alkaline Phosphatase Kit (Sigma, Cat. No. 104-LL). Preferably, cells are washed once with 200 μl PBS+Ca, Mg, 100 μl Alkaline Buffer Solution is added to each well and the cells are incubated at 37° C. for 10 minutes. 100 μl Substrate Solution is subsequently added to each well and the plate is incubated at 37° C. for 30 min. 100 μl 2.0 N NaOH is added to each well to stop the reaction. Absorbance is measured using a plate reader at 405 nm.

Agonist compounds according to the invention would provide an increase in alkaline phosphatase production relative to isotonic saline, preferably, at least about 10% increase in alkaline phosphatase production relative to isotonic saline, and still more preferably a 15% or greater increase in alkaline phosphatase production relative to isotonic saline. The increase in production of alkaline phosphatase is a measure for increased activity of osteoblasts and accordingly a measure for an increase in bone formation.

Still other assays may be performed to identify compounds which elicit substantially the same physiological responses as the antiarrhythmic peptides AAP, AAP10, HP, and their functional analogues (e.g., to identify agonists) or which inhibit or suppress these physiological responses (e.g., to identify antagonists). Suitable assays include, but are not limited to: assays to measure cAMP formation in cells (e.g., CHO cells); cAMP efficacy assays (e.g., measuring inhibition of forskoline-stimulated cAMP formation of APP-like compounds in CHO cells); phosphoinositol turnover in cardiomyocytes (Meier et al.) (E. Meier, et al. (1997) Drug Development Research, 40: 1-16); and responses to glucose and oxygen deprivation.

A number of standard assays are detailed above. Additional assays are described in WO02/77017 (PCT/US02/05773), the entirety of which is incorporated herein by reference. These assays are exemplary only and other suitable assays that may be developed and become standardized are encompassed within the scope of the invention.

Preparation of the Compounds

It is preferred to synthesize the N- or C-terminally modified small peptide compounds of the invention by means of solid phase or liquid phase peptide synthesis. In this context, reference is given to WO 98/11125 and, amongst many others, Fields, G B et al., 2002, "Principles and practice of solid-phase peptide synthesis". In: Synthetic Peptides (2nd Edition) and the Examples herein.

Pharmaceutical Compositions

The present invention also concerns a pharmaceutical composition comprising one or more of any of the compounds described above, in combination with a pharmaceutically acceptable carrier and/or diluent.

Route of Administration

The compounds of the present invention may serve as medicaments in their pure form or as pharmaceutical compositions and they may be administered via any of the usual and acceptable methods known in the art, either singly or in combination. Such compositions may be formulated to oral administration (including buccal cavity or sublingually) or by parenteral administration (including intravenous (i.v.), subcutaneous (s.c.), intramuscular (i.m.), intraperitoneal (i.p.)) administration. Other administration routes include epidural, rectal, intranasal or dermal administration or by pulmonary inhalation.

Types of Formulations

The present invention contemplates a pharmaceutical composition comprising, as an active principle, a compound of the invention in admixture with a pharmaceutically acceptable carrier, diluent, vehicle or excipient. Typically, such a pharmaceutical composition will be a dose form selected from the group consisting of an oral dosage form, a buccal dosage form, a sublingual dosage form, an anal dosage form, and a parenteral dosage form such as an intravenous, an intraarterial, an intraperitoneal, a subdermal, an intradermal or an intracranial dosage form. Especially preferred formulations provide sustained release of the peptide of the invention.

The compositions may preferably be formulated to subcutaneous administration, and such compositions may be prepared in a manner well known to the field. The compositions are preferably in the form of solid or liquid formulations and methods for their preparation are generally described in "Remington's Pharmaceutical Sciences", 17th Ed., Alfonso R. Gennaro (Ed.), Mark Publishing Company, Easton, Pa., U.S.A., 1985. Solutions are most useful for injection or infusion (i.v., s.c., i.m., or i.p.) or intranasal administration.

Such compositions will contain an effective amount of the one or more active compounds of this invention together with a suitable carrier in order to provide the dosage in a form compatible with the route of administration selected. The compositions comprising at least one of the compounds of this invention together with a physiologically acceptable carrier in the form of a vehicle, a diluent, a buffering agent, a tonicity adjusting agent, a preservative and stabilizers. The excipients constituting the carrier must be compatible with the active pharmaceutical ingredient(s) and preferably capable of stabilizing the compounds without being deleterious to the subject being treated.

Depot (Sustained Release) Formulations

In a preferred embodiment of the invention depot formulations that include at least one of the present compounds are envisioned. A form of repository or depot formulation may be used so that therapeutically effective amounts of the preparation are delivered into the bloodstream over many hours or days following transdermal injection or deposition. Formulations suitable for sustained release formulations include biodegradable polymers and may consist of appropriate biodegradable polymers, such as L-lactic acid, D-lactic acid, DL-lactic acid, glycolide, glycolic acid, and any isomers thereof. Similarly, the carrier or diluent may include any sustained release material known in the art, such as glyceryl monostearate or glyceryl distearate, alone or mixed with a wax.

Other depot formulations may include, but are not limited to, formulations that include at least one of the present compounds disclosed herein combined with liposomes, microspheres, emulsions or micelles and liquid stabilizers.

Doses

The doses the compounds and compositions of the present invention required for the desired therapeutic effects will depend upon on the potency of the compound, the particular composition used and the route of administration selected. The compounds will typically be administered in the range of about 0.001 to 10 g per patient per day, preferably from about 1 to about 1000 mg per patient per day, more preferably from about 10 to about 100 mg per patient per day, about 50 mg per patient per day. Dosages for certain routes, for example non-parenteral administration routes, should be increased to account for any decreased bioavailability, for example, by about 5-100 fold.

Dosing Regimen

The most suitable dosing regimen may best be determined by a medical practitioner for each patient individually. The optimal dosing regimen with the compounds and pharmaceutical compositions of this invention depends on factors such as the particular disease or disorder being treated, the desired effect, and the age, weight or body mass index, and general physical conditions of the patient. The administration may be conducted in a single unit dosage form to alleviate acute symptoms or as a continuous therapy in the form of multiple doses over time. Alternatively, continuous infusion systems or slow release depot formulations may be employed. Two or more compounds or pharmaceutical compositions of this invention may be co-administered simultaneously or sequentially in any order. In addition, the compounds and compositions may be administered in a similar manner for prophylactic purposes. Ultimately, the best dosing regimen will be decided by the attending physician for each patient individually.

The following non-limiting examples are presented merely in order to illustrate the invention. The skilled person in the area will understand that there are numerous equivalents and variations not exemplified but still forming part of the present invention.

Use of the Compounds in Disease Treatment

In one aspect, the invention provides a method of administering to a subject having, or at risk of developing, a condition associated cardiac arrhythmia, osteoporosis or with impaired GJIC, a therapeutically effective amount of any of the compounds described above. Individuals who may be treated using compounds according to the invention include, but are not limited to, animals, preferably mammals, e.g., rodents (including mice, rats, hamsters, and lagomorphs, such as rabbits), dogs, pigs, goats (generally any domestic animal), and primates. In one preferred aspect, the subject is a human being. Examples of conditions which can be treated include, but are not limited to, cardiovascular disease, inflammation of airway epithelium, disorders of alveolar tissue, bladder incontinence, impaired hearing due to diseases of the cochlea, endothelial lesions, diabetic retinopathy and diabetic neuropathy, ischemia of the central nervous system and spinal cord, dental tissue disorders including periodontal disease, kidney diseases, failures of bone marrow transplantation, wounds, erectile dysfunction, urinary bladder incontinence, neuropathic pain, subchronic and chronic inflammation, cancer and failures of bone marrow and stem cell transplantation, conditions which arise during transplantation of cells and tissues or during medical procedures such as surgery; as well as conditions caused by an excess of reactive oxygen species and/or free radicals and/or nitric oxide.

In one preferred aspect, the invention provides a pharmacologically active antiarrhythmic compound, and the use thereof, for treatment of arrhythmias and thrombotic complications arising during cardiovascular disorders, such as acute ischemic heart disease (e.g., stable angina pectoris, unstable angina pectoris, acute myocardial infarction), congestive heart failure (e.g., systolic, diastolic, high-output, low-output, right or left sided heart failure), congenital heart diseases, cor pulmonale, cardiomyopathies, myocarditis, hypertensive heart disease, during coronary revascularization, and the like. In specific embodiments, an antiarrhythmic compound according to the present invention is used to treat and/or prevent bradyarrhythmias (e.g., due to disease in sinus node, AV node, bundle of His, right or left bundle branch), and tachyarrhythmias associated with reentry (e.g., atrial premature complexes, AV junctional complexes, ventricular premature complexes, atrial fibrillation, atrial flutter, paroxymal supraventricular tachycardia, sinus node reentrant tachycardia, AV nodal reentrant tachycardia, and non-sustained ventricular tachycardia) either alone or in combination with other antiarrhythmic compounds, such as class I agents (e.g., lidocaine), class II agents (e.g., metoprolol or propranolol), class III agents (e.g., amiodarone or sotalol) or class IV agents (e.g., verapamil).

Additionally, or alternatively, compounds according to the invention are used to treat one or more of: a reentry arrhythmia; ventricular reentry (e.g., such as arises during acute myocardial infarction, chronic myocardial infarction, stable angina pectoris and unstable angina pectoris); infectious or autonomic cardiomyopathy; atrial fibrillation; repolarization alternans; monomorphic ventricular tachycardia; T-wave alternans; bradyarrhythmias; and generally, reduced contractility of cardiac tissue, thrombosis and the like.

Osteoporosis

In a further aspect, compounds according to the invention are used to prevent and/or treatment of osteoporosis or other pathologies affecting bone formation, growth or maintenance. Compounds which are able to normalize the attenuated GJIC between human osteoblast during hypoxia are particularly suitable for the treatment of bone diseases with impaired bone formation relative to bone resorption. Compounds for use in such methods can be selected in assays for increased alkaline phosphatase (ALP) activity in osteoblasts, which provides a means to monitor cell viability and growth as a consequence of proper maintenance of GJIC. In one aspect, human osteoblasts are stimulated with different concentrations of compounds from $1 \times 10^{-13}$ to $1 \times 10^{-6}$ mol/l, and compared to untreated controls. Under normal culture conditions, compounds preferably increase ALP activity. Preferably, the compounds also stimulate ALP activity during hypoxic conditions, such as at concentrations ranging from $10^{-11}$ to $10^{-8}$ mol/l. The assay can thus be used to optimize compound compositions for the treatment and/or prevention of bone diseases associated with poor vascularization, hypoxia and ischemia in bone tissue.

Ischemia

Additional functions in which endothelial gap-junctional intercellular communication has been implicated are the migratory behavior of endothelial cells after injury, angiogenesis, endothelial growth and senescence, and the coordination of vasomotor responses (G. J. Christ, et al. (2000) *Braz. J Med Biol. Res.*, 33: 423-429). Therefore, in one aspect, a compound according to the invention is used to enhance conducted vascular responses and to improve blood supply during conditions with increased metabolic demand (e.g., physical exercise, tachycardia), and during ischemia.

It should be obvious to those of skill in the art, that the compounds and pharmaceutical compositions according to the invention can be used to treat any condition or pathology including those associated with impaired (abnormal decreases or increases in) gap junctional communication. Preferably, one or more of the compounds or pharmaceutical compositions comprising the one or more compounds are administered to an individual in need thereof in a therapeutically effective amount. As used herein, "a therapeutically effective amount" is one which reduces symptoms of a given condition or pathology, and preferably which normalizes physiological responses in a subject with the condition or pathology. Reduction of symptoms or normalization of physiological responses can be determined using methods routine in the art and may vary with a given condition or pathology. In one aspect, a therapeutically effective amount of one or more compounds or pharmaceutical composition comprising the one or more compounds is an amount which restores a measurable physiological parameter to substantially the same value (preferably to within ±30%, more preferably to within ±20%, and still more preferably, to within 10% of the value) of the parameter in a subject without the condition or pathology.

The effective amount will be determined by the skilled person taking into account such factors as potency of the drug, age and constitution of the patient, body weight, pharmacokinetic profile of the drug, and in general the drug will be prescribed for each patient or group of patients. However, the effective amount of the compound is preferably at least about 10 μg/kg body weight/day, such as at least 100 μg/kg body weight/day, at least 300 μg/body weight/day, and at least 1000 μg/kg body weight/day. On the other hand, the effective amount of the compound or dimer is preferably at most about 100 mg/kg body weight/day, such as at most 50 mg/kg body weight/day and at most 10 mg/kg body weight/day. It is expected that the effective amount of the compound will be about 100 μg/kg body weight/day, about 300 μg/kg body weight/day or about 1000 μg/kg body weight.

EXPERIMENTAL SECTIONS

The invention will now be further illustrated with reference to the following non-limiting examples. It will be appreciated that what follows is by way of example only and that modifications to detail may be made while still falling within the scope of the invention.

Example 1

Compound Synthesis

A preferred general peptide synthesis procedure is described below. However, more detailed descriptions of solid phase peptide syntheses are found in WO98/11125 hereby incorporated by reference in its entirety.

General Peptide Synthesis

Apparatus and Synthetic Strategy

Peptides were synthesized batchwise in a polyethylene vessel equipped with a polypropylene filter for filtration using 9-fluorenylmethyloxycarbonyl (Fmoc) as N-α-amino protecting group and suitable common protection groups for side-chain functionalities.

Solvents

Solvent DMF (N,N-dimethylformamide, Riedel de-Häen, Germany) was purified by passing through a column packed with a strong cation exchange resin (Lewatit S 100 MB/H strong acid, Bayer AG Leverkusen, Germany) and analyzed for free amines prior to use by addition of 3,4-dihydro-3-hydroxy-4-oxo-1,2,3-benzotriazine (Dhbt-OH) giving rise to a yellow color (Dhbt-O⁻ anion) if free amines are present. Solvent DCM (dichloromethane, analytical grade, Riedel de-Häen, Germany) was used directly without purification. Acetonitril (HPLC-grade, Lab-Scan, Dublin Ireland) was used directly without purification.

Amino Acids

Fmoc-protected amino acids were purchased from Advanced ChemTech (ACT), Bachem and NeoSystem in suitable side-chain protected or derivatised forms.

Aryl and Other Reagents for Terminal Modification

All reagents used for terminal modification were purchased from Aldrich and used without further purification.

Coupling Reagents

Coupling reagent diisopropylcarbodiimide (DIC) was purchased from (Riedel de-Häen, Germany), PyBop from Advanced ChemTech.

Linkers (4-hydroxymethylphenoxy)acetic acid (HMPA), was purchased from Novabiochem, Switzerland; and was coupled to the resin as a preformed 1-hydroxybenzotriazole (HOBt) ester generated by means of DIC.

Solid Supports

Peptides synthesized according to the Fmoc-strategy on TentaGel S resins 0.22-0.31 mmol/g (TentaGel-S—NH₂; TentaGel S-Ram, Rapp polymere, Germany).

Catalysts and Other Reagents

Diisopropylethylamine (DIEA) was purchased from Aldrich, Germany, and ethylenediamine from Fluka, piperidine and pyridine from Riedel-de Häen, Frankfurt, Germany. 4-(N,N-dimethylamino)pyridine (DMAP) was purchased from Fluka, Switzerland and used as a catalyst in coupling reactions involving symmetrical anhydrides. Ethanedithiol was purchased from Riedel-de Häen, Frankfurt, Germany. 3,4-dihydro-3-hydroxy-4-oxo-1,2,3-benzotriazine (Dhbt-OH), 1-hydroxybenzotriazole (HOBt) (HOAt) were obtained from Fluka, Switzerland.

Coupling Procedures

The first amino acid can be coupled as a symmetrical anhydride in DMF generated from the appropriate N-α-protected amino acid and the subsequent amino acids can be coupled as in situ generated HOBt or HOAt esters made from appropriate N-α-protected amino acids and HOBt or HOAt by means of DIC in DMF. The acylations were checked by the ninhydrin test performed at 80° C. in order to prevent Fmoc deprotection during the test (B. D. Larsen, A. Holm, Int. J Pept. Protein Res. 1994, 43 1-9).

Deprotection of the N-α-Amino Protecting Group (Fmoc)

Deprotection of the Fmoc group was performed by treatment with 20% piperidine in DMF (1×5 and 1×10 min.), followed by wash with DMF (5×15 ml, 5 min. each) until no yellow color could be detected after addition of Dhbt-OH to the drained DMF.

Deprotection of Allyl/Aloc

A solution of 3 eq. Pd(PPh$_3$)$_4$ dissolved in 15-20 ml CHCl$_3$, AcOH, NMM (37:2:1) was added to the peptide resin. The treatment was continued for three hours at room temperature accompanied by bubbling a stream of N$_2$ through the mixture.

Coupling Of HOBt-Esters 3 eq. N-α-amino protected amino acid was dissolved in DMF together with 3 eq. HOBt and 3 eq. DIC and then added to the resin.

Preformed Symmetrical Anhydride

Six eq. N-α-amino protected amino acid was dissolved in DCM and cooled to 0° C. DIC (3 eq.) was added and the reaction continued for 10 minutes. The solvent was removed in vacuo and the remanence dissolved in DMF. The solution was immediately added to the resin followed by 0.1 eq. of DMAP.

Cleavage of Peptide from Resin with Acid

Peptides were cleaved from the resins by treatment with 95% trifluoroacetic acid (TFA, Riedel-de Häen, Frankfurt, Germany)-water v/v or with 95% TFA and 5% ethanedithiol v/v at r.t. for 2 hours. The filtered resins were washed with 95% TFA-water and filtrates and washings evaporated under reduced pressure. The residue was washed with ether and freeze-dried from TFA-water. The crude freeze-dried product was analyzed by high-performance liquid chromatography (HPLC) and identified by electrospray ionisation mass spectrometry (ESMS).

Batchwise Peptide Synthesis on TentaGel Resin (PEG-PS)

TentaGel resin (1 g, 0.22-0.31 mmol/g) was placed in a polyethylene vessel equipped with a polypropylene filter for filtration. The resin was swelled in DMF (15 ml), and treated with 20% piperidine in DMF to secure the presence of non-protonated amino groups on the resin. The resin was drained and washed with DMF until no yellow color could be detected after addition of Dhbt-OH to the drained DMF. HMPA (3 eq.) was coupled as a preformed HOBt-ester as described above and the coupling was continued for 24 h. The resin was drained and washed with DMF (5×5 ml, 5 min each) and the acylation checked by the ninhydrin test. The first amino acid was coupled as a preformed symmetrical anhydride as described above. The following amino acids according to the sequence were coupled as preformed Fmoc-protected HOBt esters (3 eq.) as described above. The couplings were continued for 2 h, unless otherwise specified. The resin was drained and washed with DMF (5×15 ml, 5 min each) in order to remove excess reagent. All acylations were checked by the ninhydrin test performed at 80° C. After completed synthesis the peptide-resin was washed with DMF (3×15 ml, 5 min each), DCM (3×15 ml, 1 min each) and finally diethyl ether (3×15 ml, 1 min each) and dried in vacuo.

Preparative HPLC Conditions.

Preparative chromatography was carried out using a VISION Workstation (PerSeptive Biosystem) equipped with AFC2000 automatic fraction collector/autosampler. VISION-3 software was used for instrument control and data acquisition.

Column

Kromasil (EKA Chemicals) KR100-10-C8 100 Å, C-8, 10 μm; CER 2230, 250×50.8 mm or a VYDAC 218TP101550, 300 Å, C-18, 10-15 μm, 250×50 mm. The buffer system used included A: 0.1% TFA in MQV; B: 0.085% TFA, 10% MQV, 90% MeCN. Flow rates were 35-40 mL/min and the column temperature was 25° C. UV detection was performed at 215 nm and 280 nm. Suitable gradients were optimized for individual peptides.

Analytical HPLC Conditions

Gradient HPLC analysis was done using a Hewlett Packard HP 1100 HPLC system consisting of a HP 1100 Quaternary Pump, a HP 1100 Autosampler a HP 1100 Column Thermostat and HP 1100 Multiple Wavelength Detector. Hewlett Packard Chemstation for LC software (rev. A.06.01) was used for instrument control and data acquisition. For analytical HPLC, different columns were used as appropriate, such as VYDAC 238TP5415, C-18, 5 μm, 300 Å, or a Jupiter, Phenomenex 00F-4053-E0; 5 μm C-18, 300 Å 150×4, 6 mm and others. The buffer system included A: 0.1% TFA in MQV; B: 0.085% TFA, 10% MQV, 90% MeCN. Flow rates were 1 mL/min. The preferred column temperature was 40° C. UV detection was performed at 215 nm. As above, suitable gradients were optimized for the individual peptides.

Mass Spectroscopy

The peptides were dissolved in super gradient methanol (Labscan, Dublin, Ireland), Milli-Q water (Millipore, Bedford, Mass.) and formic acid (Merck, Damstadt, Germany) (50:50:0.1 v/v/v) to give concentrations between 1 and 10 μg/mL. The peptide solutions (20 μl) were analysed in positive polarity mode by ESI-TOF-MS using a LCT mass spectrometer (Micromass, Manchester, UK) accuracy of +/−0.1 m/z.

General Synthetic Procedure

Peptide Synthesis Procedure a)

| | |
|---|---|
| Compound 1 | 7HC4A-Asn-Gly-NH$_2$ |
| Compound 2 | HAA-Gly-Tyr-NH$_2$ |
| Compound 3 | HAA-Gln-Tyr-NH$_2$ |
| Compound 4 | Fmoc-Asn-Gly-NH$_2$ |
| Compound 5 | (Acridin-9-carbonyl)-Asn-Gly-NH$_2$ |
| Compound 6 | (Pyrenyl-1-carboxyl)-Asn-Gly-NH$_2$ |
| Compound 7 | Thiohydroxyacetyl-Asn-Tyr-NH$_2$ |
| Compound 8 | N-((Acetylhydroxy)acetyl)-Asn-Tyr-NH$_2$ |

TentaGel resin (0.22-0.31 mmol/g) was placed in a polyethylene vessel equipped with a polypropylene filter for filtration. The resin was swelled in DMF, and treated with 20% piperidine in DMF to secure the presence of non-protonated amino groups on the resin. The resin was drained and washed with DMF until no yellow color could be detected after addition of Dhbt-OH to the drained DMF. The amino acids according to the sequence were coupled as preformed Fmoc-protected HOBt esters as described above. The couplings were continued for 2 h, unless otherwise specified. The resin was drained and washed with DMF in order to remove excess reagent. All acylations were checked by the ninhydrin test performed at 80° C. The N-terminal amino group was subsequent modified by coupling of a suitable protected carboxylic acid derivative of the individual modification reagents as a preformed HOBt ester as described above.

After completed synthesis the N-terminal modified peptide-resin was washed with DMF, DCM and finally diethyl ether and dried in vacuo.

The peptide was then cleaved from the resin as described above and freeze-dried.

After purification using preparative HPLC as described above, the peptide product was collected and the identity of the peptide was confirmed by ES-MS.

Peptide Synthesis Procedure b)

| Compound 9 | H-Gly-Asn-7A4MC |
| Compound 10 | H-Gly-Asn-NH-(4-nitrophenyl)) |
| Compound 11 | Ac-Gly-Asn-NH(pNO$_2$-Phenyl) |

TentaGel resin (0.22-0.31 mmol/g) was placed in a polyethylene vessel equipped with a polypropylene filter for filtration. The resin was swelled in DMF and treated with 20% piperidine in DMF to secure the presence of non-protonated amino groups on the resin. The resin was drained and washed with DMF until no yellow color could be detected after addition of Dhbt-OH to the drained DMF. The C-terminal amino acid Asparagine was coupled as Fmoc-Aso-PNA or Fmoc-Asp-AMC according to the sequence. The following amino acids according to the sequence were coupled as preformed Fmoc-protected HOBt esters as described above. All couplings were continued for 2 h, unless otherwise specified. The resin was drained and washed with DMF in order to remove excess reagent. After deprotection of the Fmoc group the N-terminal amino group according to the sequence was either left as so or was acetylated with acetic acid anhydride together with pyridine in DMF or with Hydroxyacetic acid coupled as a preformed HOBt ester as described above. All acylations were checked by the ninhydrin test performed at 80° C.

After completed synthesis the peptide-resin was washed with DMF, DCM and finally diethyl ether and dried in vacuo.

The peptide was then cleaved from the resin as described above and freeze-dried.

After purification using preparative HPLC as described above, the peptide product was collected and the identity of the peptide was confirmed by ES-MS.

Peptide Synthesis Procedure c)

| Compound 12 | H-Gly-Asn-NH-(1-pyrenyl) |
| Compound 13 | AcGly-Asn-NH(pyrenylmethyl) |
| Compound 14 | N-(acetyl)-Gly-Asn-NH(quinolin-6-yl) |

TentaGel resin (0.22-0.31 mmol/g) was placed in a polyethylene vessel equipped with a polypropylene filter for filtration. The resin was swelled in DMF and treated with 20% piperidine in DMF to secure the presence of non-protonated amino groups on the resin. The resin was drained and washed with DMF until no yellow color could be detected after addition of Dhbt-OH to the drained DMF. The C-terminal amino acid Asparagine was coupled as Fmoc-Asp-Oall. The O-allyl group was removed as described above. The hydrophobic group functionalised as an amine was coupled to the pre generated HOBt ester of the deprotected carboxylic acid by means of DIC in DMF catalyzed by triethylamine. After subsequent Fmoc-deprotection the following amino acids according to the sequence were coupled as preformed Fmoc-protected HOBt esters as described above. All couplings were continued for 2 h, unless otherwise specified. The resin was drained and washed with DMF in order to remove excess reagent. After deprotection of the Fmoc group the N-terminal amino group according to the sequence was either left as so or was acetylated with acetic acid anhydride together with pyridine in DMF. All acylations were checked by the ninhydrin test performed at 80° C.

After completed synthesis the peptide-resin was washed with DMF, DCM and finally diethyl ether and dried in vacuo.

The peptide was then cleaved from the resin as described above and freeze-dried.

After purification using preparative HPLC as described above, the peptide product was collected and the identity of the peptide was confirmed by ES-MS.

Peptide Synthesis Procedure d)

| Compound 15 | (7HC4A)-D-Asn-Gly-OH |

Dry TentaGel-S—NH$_2$ (0.23 mmol/g) was placed in a polyethylene vessel equipped with a polypropylene filter for filtration and treated as described under "batchwise peptide synthesis on TentaGel resin." The C-terminally Glycine was coupled as symmetrically anhydride according to the procedure described above.

The following amino acid according to the sequence was coupled as preformed Fmoc-protected HOBt ester as described above. All couplings were continued for 2 h, unless otherwise specified. The resin was drained and washed with DMF in order to remove excess reagent. All acylations were checked by the ninhydrin test performed at 80° C. The N-terminal amino group was subsequent modified by coupling of a suitable protected carboxylic acid derivative of the individual modification reagents as a preformed HOBt ester as described above.

After completed synthesis the N-terminal modified peptide-resin was washed with DMF, DCM and finally diethyl ether and dried in vacuo.

The peptide was then cleaved from the resin as described above and freeze-dried.

After purification using preparative HPLC as described above, the peptide product was collected and the identity of the peptide was confirmed by ES-MS.

Synthesis of Individual Peptides

Synthesis of N-(7-hydroxycoumarin-4-acetyl)-Asn-Gly-NH$_2$ (Compound 1)

The N-terminal modified peptide N-(7-Hydroxycoumarin-4-acetyl)-Asn-Gly-NH$_2$ was synthesised according to procedure a) and the identity of the product was confirmed by ES-MS (found MH$^+$ 390.12, calculated MH$^+$ 390.26).

Synthesis of N-(hydroxyacetyl)-Gly-Tyr-NH$_2$ (Compound 2)

The N-terminal modified peptide N-(hydroxyacetyl)-Gly-Tyr-NH$_2$ was synthesised according to procedure a) and the identity of the product was confirmed by ES-MS (found MH$^+$ 295.06, calculated MH$^+$ 295.15).

Synthesis of N-(hydroxyacetyl)-Gln-Tyr-NH$_2$ (Compound 3)

The N-terminal modified peptide N-(hydroxyacetyl)-Gln-Tyr-NH$_2$ was synthesised according to procedure a) and the identity of the product was confirmed by ES-MS (found MH$^+$ 366.10, calculated MH$^+$ 366.19).

Synthesis of N-(9-fluorenylmethyloxycarbonyl)-Asn-Gly-NH$_2$ (Compound 4)

The N-terminal modified peptide N-(9-Fluorenylmethyloxycarbonyl)-Asn-Gly-NH$_2$ was synthesised according to procedure a) and the identity of the product was confirmed by ES-MS (found MH$^+$ 410.06, calculated MH$^+$ 410.16).

Synthesis of N-(acridin-9-carbonyl)-Asn-Gly-NH$_2$ (Compound 5)

The N-terminal modified peptide N-(Acridin-9-carbonyl)-Asn-Gly-NH$_2$ was synthesised according to procedure a) and the identity of the product was confirmed by ES-MS (found MH$^+$ 393.22, calculated MH$^+$ 393.31).

Synthesis of N-(pyrenyl-1-carbonyl)-Asn-Tyr-NH$_2$ (Compound 6)

The N-terminal modified peptide N-(Pyrenyl-1-carbonyl)-Asn-Tyr-NH$_2$ was synthesised according to procedure a) and the identity of the product was confirmed by ES-MS (found MH$^+$ 416.18, calculated MH$^+$ 416.35).

Synthesis of N-(thiohydroxyacteyl)-Asn-Tyr-NH$_2$ (Compound 7)

The N-terminal modified peptide N-(Thiohydroxyacetyl)-Asn-Tyr-NH$_2$ was synthesised according to procedure a) and the identity of the product was confirmed by ES-MS (found MH$^+$ 368.11, calculated MH$^+$ 368.23).

Synthesis of N-((acetylhydroxy)acetyl))-Asn-Tyr-NH$_2$ (Compound 8)

The N-terminal modified peptide N-((acetylhydroxy)acetyl)-Asn-Tyr-NH$_2$ was synthesised according to procedure a) and the identity of the product was confirmed by ES-MS (found MH$^+$ 394.05, calculated MH$^+$ 394.17).

Synthesis of H-Gly-Asn-NH(4-methyl-coumarin-7-yl) (Compound 9)

The C-terminal modified peptide H-Gly-Asn-NH(4-methyl-coumarin-7-yl) was synthesised according to procedure b) and the identity of the product was confirmed by ES-MS (found MH$^+$ 346.20, calculated MH$^+$ 346.24).

Synthesis of H-Gly-Asn-NH(4-nitrophenyl) (Compound 10)

The C-terminal modified peptide H-Gly-Asn-NH(4-nitrophenyl) was synthesised according to procedure b) and the identity of the product was confirmed by ES-MS (found MH$^+$ 309.11, calculated MH$^+$ 309.17).

Synthesis of Ac-Gly-Asn-NH(4-nitrophenyl) (Compound 11)

The acetylated and C-terminal modified peptide Ac-Gly-Asn-NH(4-nitrophenyl) was synthesised according to procedure b) and the identity of the product was confirmed by ES-MS (found MH$^+$ 351.09, calculated MH$^+$ 351.18).

Synthesis of H-Gly-Asn-NH(pyrenylmethyl) (Compound 12)

The C-terminal modified peptide H-Gly-Asn-NH(pyrenylmethyl) was synthesised according to procedure c) and the identity of the product was confirmed by ES-MS (found MH$^+$ 402.27, calculated MH$^+$ 402.39).

Synthesis of Ac-Gly-Asn-NH(pyrenylmethyl) (Compound 13)

The acetylated and C-terminal modified peptide Ac-Gly-Asn-NH(pyrenylmethyl) was synthesised according to procedure c) and the identity of the product was confirmed by ES-MS (found MH$^+$ 444.32, calculated MH$^+$ 444.4).

Synthesis of Ac-Gly-Asn-NH(quinolin-6-yl) (Compound 14)

The acetylated and C-terminal modified peptide Ac-Gly-Asn-NH(quinolin-6-yl) was synthesised according to procedure c) and the identity of the product was confirmed by ES-MS (found MH$^+$ 357.19, calculated MH$^+$ 357.27).

Synthesis of N-(7-hydroxycoumarin-4-acetyl)-D-Asn-Gly-OH (Compound 15)

The acetylated and C-terminal modified peptide N-(7-hydroxycoumarin-4-acetyl)-D-Asn-Gly-OH was synthesised according to procedure d) and the identity of the product was confirmed by ES-MS (found MH$^+$ 391.18, calculated MH$^+$ 391.25).

Example 2

Effect of the Compounds on Calcium Induced Arrhythmias

The anti-arrhythmic effect of the present compounds was tested in a model of calcium-induced arrhythmias according to the model of Lynch et al., *J. Cardiovasc. Pharmacol.* (1981), 3: 49-60. Male NMRI mice (25-30 grams; Bomholdtgaard, L I. Skendsved, Denmark) were anesthetized with a neurolept anesthetic combination (Hynorm® (fentanyl citrate 0.315 mg/mL and fuanisone 10 mg/mL) and midazolam at 5 mg/mL. Commercial solutions of Hynorm® and midazolam were diluted 1:1 in distilled water, and one part Hynorm® was mixed with one part diluted midazolam. Anesthesia is induced by s.c. administration of this solution in a dose of 50-75 µL/10 gram mouse.

An intravenous cannula was inserted into the tail vein. The lead II ECG signal was recorded continuously by positioning of stainless steel ECG electrodes on the right forelimb and on the left hind limb. The ground electrode was placed on the right hind limb. The signal was amplified (×5.000-10.000) and filtered (0.1-150 Hz) via a Hugo Sachs Electronic model 689 ECG module. The analogue signal was digitized via a 12-bit data acquisition board (Data Translation model DT321) and sampled at 1000 Hz using the Notocord HEM 3.1 software for Windows NT. After a 10-min equilibration period, the test sample of compound was injected into the tail vein at a dose of 1 nmol/kg and three minutes later intravenous infusion of $CaCl_2$ (30 mg/mL, 0.1 mL/min~100 mg/kg/min, calcium chloride-2-hydrate, Riedel-de Haen, Germany) was started.

Mice pre-treated with vehicle (phosphate buffered saline with 0.1% bovine albumin) were tested on all days as a measure for control level in untreated animal. Injection volume was 100 μL in all experiments. The time lag to onset of arrhythmias was determined as the time from the start of $CaCl_2$ infusion until the first event of conduction block (defined as intermittent failure of the SA or AV conduction characterized by delayed P-wave activation (SA block) or by a P-wave without the concomitant QRS complex (AV block). The % response of the tested compounds is given below in Table 2. The response is estimated according to ($t_{arr}$ (test compound)–$t_{arr}$ (vehicle))×100/$t_{arr}$ (vehicle).

TABLE 2

($CaCl_2$ data)

| Compound No | Compound name | % response |
|---|---|---|
| 1 | N-(7-hydroxycoumarin-4-acetyl)-Asn-Gly-$NH_2$ | 20.9 |
| 2 | N-(hydroxyacetyl)-Gly-Tyr-NH2 | 48.7 |
| 8 | N-((Acetylhydroxy)acetyl))-Asn-Tyr-$NH_2$ | 16.5 |
| 10 | H-Gly-Asn-NH(4-nitrophenyl) | 38.0 |
| 12 | H-Gly-Asn-NH(pyrenylmethyl) | 38.0 |
| 15 | N-(7-hydroxycoumarin-4-acetyl)-D-Asn-Gly-OH | 28.5 |

It follows from the data presented in Table 2 that pretreatment of a mouse with a range of compounds of the invention resulted in a consistent increase in the time to an AV block in the mouse after infusion of $CaCl_2$. The compounds of the invention thus exhibit antiarrhythmic properties.

Example 3

Pharmacokinetic Properties of the Compounds

The compounds of the invention show desirable pharmacokinetic profiles as evidenced from data obtained when testing the permeability of the compounds across a synthetic biomimetic membrane that resembles the blood brain barrier (PAMPA-BBB) and the compounds ability to inhibit the activity of cytochrome P 450 oxidase isozyme 3A4. Normally it is desirous to avoid having drugs targeting the cardiovascular systems and other non-CNS ailments such as osteoporosis being less able to cross the blood brain barrier and thus penetrate into the central nervous system.

Cytochrome P450 enzymes (CYPs) constitute a superfamily of heme proteins involved in the metabolism of endogenous and exogenous compounds in living organisms. In particular, a number of CYP isozymes are important in the oxidative metabolism of drug molecules. Interactions with these enzymes could lead to altered pharmacokinetic parameters, such as half life, Cmax, or AUC of other co-administered drug molecules. To reduce this kind of interaction in vitro screening of drug candidates for inhibition of drug-metabolizing CYPs has been carried out. Data are shown in Table 3 below.

Permeability test: Compounds in DMSO solution are added to pH 7.4 buffer in a 96 well plate ("donor"). The buffer is placed in contact with a 96 well filter plate in which the pours have been filled with an artificial membrane (2% phosphatidyl choline in dodecane). The top wells of the filter plate are filled with aqueous buffer ("acceptor"). Compound molecules diffuse into the artificial membrane and then into the acceptor buffer. After a 14 hr diffusion experiment, the donor and acceptor wells are measured on a UV plate reader and compared to a standard. The experiment is termed "PAMPA". Permeability-BBB: The PAMPA experiment above is repeated using brain lipid (20% in dodecane) to provide a prediction of blood-brain barrier permeation by passive diffusion.

Cytochrome P oxidase (CYP) Inhibition: The compound solution is added to a mixture of recombinant human CYP isozymes, NADPH regenerating solution, buffer, and "probe" compounds for each isozyme. The degree of reduction in the rate of metabolism of the probe to a fluorescent metabolite is an indication of the potential CYP inhibition of the test compound. The CYP 450 isozyme tested is 3A4.

TABLE 3

| Comp. No. | Sequence/Name | PAMPA-BBB ($10^{-6}$ cm/s) | CYP450 Inhibition at 3 μM (% Inhibition) CYP 3A4 |
|---|---|---|---|
| 8 | N-((acetylhydroxy)acetyl)-Asn-Tyr-$NH_2$ | 0 | <15 |
| 10 | H-Gly-Asn-[NH-4-nitrophenyl] | 0 | <15 |
| 12 | H-Gly-Asn-[NH-1-pyrenylmethyl] | 0 | <15 |
| 7 | Thiohydroxyacetyl-Asn-Tyr-$NH_2$ | 0 | <15 |
| 16 | [Methoxyacetyl]-NY-$NH_2$ | 0 | <15 |
| Comp. No. WO2004/048400 | | | |
| 23 | H-DLys(benzoyl)-G-OH | NA | 15–25 |
| 8 | H-K(4-nitrobenzoyl)-Sar-OH | NA | 15–25 |
| 80 | H-Asn(4-methoxybenzyl)-DAla-OH | NA | 15–25 |
| 7 | H-K(4-nitrobenzoyl)-G-OH | NA | 15–25 |

It follows from the data presented in Table 3 that a range of compounds of the invention does not penetrate the PAMPA-BBB synthetic membrane. In addition, the same range of compounds of the invention shows significantly less inhibition of CYP 3A4 (<15%) compared to the compounds of WO 2004/048400 which show from 15 to 25% inhibition.

All patents, patent applications, and publications mentioned in this specification are herein incorporated by reference to the same extent as if each independent patent, patent application, or publication was specifically and individually indicated to be incorporated by reference.

What is claimed is:

1. A compound selected from the group consisting of:
N-(7-hydroxycoumarin-4-acetyl)-Asn-Gly-$NH_2$ (Compound 1),
N-(9-fluorenylmethyloxycarbonyl)-Asn-Gly-$NH_2$ (Compound 4),
N-(acridin-9-carbonyl)-Asn-Gly-$NH_2$ (Compound 5),
N-(pyrenyl-1-carbonyl)-Asn-Tyr-$NH_2$ (Compound 6),
H-Gly-Asn-NH(4-methyl-coumarin-7-yl) (Compound 9),
H-Gly-Asn-NH(4-nitrophenyl) (Compound 10),
Ac-Gly-Asn-NH(4-nitrophenyl) (Compound II), H-Gly-Asn-NH(pyrenylmethyl) (Compound 12),
Ac-Gly-Asn-NH(pyrenylmethyl) (Compound 13),
Ac-Gly-Asn-NH(quinolin-6-yl) (Compound 14), and
N-(7-hydroxycoumarin-4-acetyl)-D-Asn-Gly-OH (Compound 15), or a pharmaceutically acceptable salt thereof.

2. The compound of claim 1, wherein said compound is N-(7-hydroxycoumarin-4-acetyl)-Asn-Gly-NH$_2$ (Compound I), or a pharmaceutically acceptable salt thereof.

3. The compound of claim 1, wherein said compound is N-(9-fluorenylmethyloxycarbonyl)-Asn-Gly-NH$_2$ (Compound 4), or a pharmaceutically acceptable salt thereof.

4. The compound of claim 1, wherein said compound is N-(acridin-9-carbonyl)-Asn-Gly-NH$_2$ (Compound 5), or a pharmaceutically acceptable salt thereof.

5. The compound of claim 1, wherein said compound is N-(pyrenyl-1-carbonyl)-Asn-Tyr-NH$_2$ (Compound 6), or a pharmaceutically acceptable salt thereof.

6. The compound of claim 1, wherein said compound is H-Gly-Asn-NH(4-methyl-coumarin-7-yl) (Compound 9), or a pharmaceutically acceptable salt thereof.

7. The compound of claim 1, wherein said compound is H-Gly-Asn-NH(4-nitrophenyl) (Compound 10), or a pharmaceutically acceptable salt thereof.

8. The compound of claim 1, wherein said compound is Ac-Gly-Asn-NH(4-nitrophenyl) (Compound 11), or a pharmaceutically acceptable salt thereof.

9. The compound of claim 1, wherein said compound is H-Gly-Asn-NH(pyrenylmethyl) (Compound 12), or a pharmaceutically acceptable salt thereof.

10. The compound of claim 1, wherein said compound is Ac-Gly-Asn-NH(pyrenylmethyl) (Compound 13), or a pharmaceutically acceptable salt thereof.

11. The compound of claim 1, wherein said compound is Ac-Gly-Asn-NH(quinolin-6-yl) (Compound 14), or a pharmaceutically acceptable salt thereof.

12. The compound of claim 1, wherein said compound is N-(7-hydroxycoumarin-4-acetyl)-D-Asn-Gly-OH (Compound 15), or a pharmaceutically acceptable salt thereof.

* * * * *

UNITED STATES PATENT AND TRADEMARK OFFICE
CERTIFICATE OF CORRECTION

PATENT NO. : 7,749,969 B2
APPLICATION NO. : 11/482365
DATED : July 6, 2010
INVENTOR(S) : Larsen et al.

It is certified that error appears in the above-identified patent and that said Letters Patent is hereby corrected as shown below:

Column 3, Line 5, replace "$C_{1-6}$alkyl;" with --$C_{1-6}$ alkyl;--;

Line 6, replace "$C_{1-6}$alkyl;" with --$C_{1-6}$ alkyl;--;

Line 8, replace "$C_{1-6}$alkyl," with --$C_{1-6}$ alkyl,--;

Line 8, replace "C (O) $C_{1-6}$alkyl;" with --C(O) $C_{1-6}$ alkyl;--.

Column 5, Line 38, replace "The term "alkenyl,"" with --The term "alkynyl,"--;

Line 44, replace "the definition of "alkenyl"" with --the definition of "alkynyl"--;

Line 46, replace "alkenyl" with --alkynyl--;

Lines 50-51, replace "alkyl, alkenyl, and alkenyl" with --alkyl, alkenyl, and alkynyl--.

Column 8, Line 10, replace "alkenyl, alkenyl, cycloalkyl," with --alkenyl, alkynyl, cycloalkyl--;

Line 23, replace "alkyl, $C_{2-6}$alkenyl" with --alkyl, $C_{2-6}$ alkenyl--;

Line 23, replace "$C_{2-6}$alkenyl, $C_{6-10}$aryl" with --$C_{2-6}$ alkynyl, $C_{6-10}$ aryl--.

Column 11, Line 59, replace "alkyl, alkenyl, alkenyl," with --alkyl, alkenyl, alkynyl--.

Column 20, Line 15, replace "Fields, G B et al." with --Fields, GB et al.--.

Column 31, Line 49, replace "compounds" with --compounds'--.

Column 32, Line 67, replace "Compound II" with --Compound 11--.

Signed and Sealed this
Thirteenth Day of March, 2012

David J. Kappos
*Director of the United States Patent and Trademark Office*